US009422262B2

(12) United States Patent
Dockendorff et al.

(10) Patent No.: US 9,422,262 B2
(45) Date of Patent: Aug. 23, 2016

(54) COMPOUNDS AND METHODS FOR TREATING DISEASES MEDIATED BY PROTEASE ACTIVATED RECEPTORS

(75) Inventors: Chris Dockendorff, Arlington, MA (US); Robert Flaumenhaft, Newton, MA (US); Lawrence MacPherson, Marlborough, MA (US)

(73) Assignees: The Broad Institute, Inc., Cambridge, MA (US); Beth Israel Deaconess Medical Center, Inc., Boston, MA (US)

( * ) Notice: Subject to any disclaimer, the term of this patent is extended or adjusted under 35 U.S.C. 154(b) by 87 days.

(21) Appl. No.: 13/825,574

(22) PCT Filed: Sep. 23, 2011
(Under 37 CFR 1.47)

(86) PCT No.: PCT/US2011/053105
§ 371 (c)(1),
(2), (4) Date: Jul. 10, 2013

(87) PCT Pub. No.: WO2012/040636
PCT Pub. Date: Mar. 29, 2012

(65) Prior Publication Data
US 2013/0331411 A1    Dec. 12, 2013

Related U.S. Application Data

(60) Provisional application No. 61/386,131, filed on Sep. 24, 2010.

(51) Int. Cl.
| C07D 333/38 | (2006.01) |
| A61K 31/381 | (2006.01) |
| C07C 233/88 | (2006.01) |
| C07D 207/34 | (2006.01) |

(Continued)

(52) U.S. Cl.
CPC .......... *C07D 333/38* (2013.01); *A61K 31/381* (2013.01); *C07C 233/88* (2013.01); *C07D 207/34* (2013.01); *C07D 213/72* (2013.01); *C07D 215/54* (2013.01); *C07D 307/68* (2013.01)

(58) Field of Classification Search
CPC .. A61K 31/38; C07C 233/88; C07D 207/34; C07D 213/72; C07D 215/54; C07D 307/68; C07D 333/38
See application file for complete search history.

(56) References Cited

U.S. PATENT DOCUMENTS

| 3,937,729 A | * | 2/1976 | Teach | 564/155 |
| 6,455,520 B1 | * | 9/2002 | Brown et al. | 514/217.11 |
| 2006/0058365 A1 | * | 3/2006 | Kohn et al. | 514/396 |

OTHER PUBLICATIONS

Han et al (Oncology Letters 2: 599-608, 2011).*

(Continued)

*Primary Examiner* — Savitha Rao
*Assistant Examiner* — Angela Brown-Pettigrew
(74) *Attorney, Agent, or Firm* — McCarter & English, LLP; Steven G. Davis

(57) ABSTRACT

The invention relates to the use of a compound of Formula I for the treatment of protease-activated receptor mediated diseases by the administration of a compound of Formula I or a prodrug or metabolite thereof.

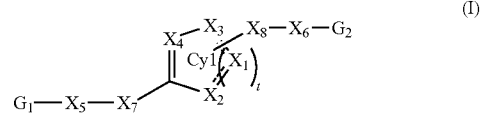

(I)

7 Claims, 5 Drawing Sheets

(51) Int. Cl.
    *C07D 213/72* (2006.01)
    *C07D 215/54* (2006.01)
    *C07D 307/68* (2006.01)

(56) References Cited

OTHER PUBLICATIONS

Ramachandran et al (Nature Reviews: Drug Discovery, vol. 11 (2012)).*

Aisiku OR, et al., 23 Effects of Biased PAR 1 Ligands on Platelets and Endothelial Cells, Presented at the 55th American Society Hematology Annual Meeting Dec. 8, 2013, New Orleans, LA.

Costanzi S. On the applicability of GPCR homology models to computer-aided drug discovery: a comparison between in silico and crystal structures of the beta2-adrenergic receptor. J Med Chem. May 22, 2008;51(10):2907-14.

Dockendorff C, et al., Discovery of 1,3-Diaminobenzenes as Selective Inhibitors of Platelet Activation at the PAR1 Receptor. ACS Med Chem Lett. Mar. 8, 2012;3(3):232-237.

Dowal L, et al., Identification of an antithrombotic allosteric modulator that acts through helix 8 of PAR1. Proc Natl Acad Sci U S A. 2011, Early Edition pp. 1-6.

Gunnink S. Allosteric of protease activated receptor 1: a new antiplatelet therapy, Verslag fellowship, 2012 pp. 1-6.

International Preliminary Report on Patentability and Written Opinion for PCT/US2011/053105, date of mailing Feb. 20, 2014.

Melnikova VO, et al., Crosstalk between protease-activated receptor 1 and platelet-activating factor receptor regulates melanoma cell adhesion molecule (MCAM/MUC18) expression and melanoma metastasis. J Biol Chem. Oct. 16, 2009;284(42):28845-55.

* cited by examiner

COMPOUNDS AND METHODS FOR TREATING DISEASES MEDIATED BY PROTEASE ACTIVATED RECEPTORS

RELATED APPLICATION

This application claims the benefit of U.S. Provisional Application No. 61/386,131, filed on Sep. 24, 2010. The entire teachings of the above application are incorporated herein by reference.

GOVERNMENT SUPPORT

The invention was supported, in whole or in part, by a grant 1R03DA026209-01 from the National Institute of Health. The Government has certain rights in the invention.

FIELD OF THE INVENTION

This invention relates to the treatment of diseases mediated by protease activated receptors.

BACKGROUND OF THE INVENTION

Protease-activated receptors (PARs) are a family of G protein-coupled receptors activated by the proteolytic cleavage of their N-terminal extracellular domain, exposing a new amino terminal sequence that functions as a tethered ligand to activate the receptors. (Zania et. al., J Pharmacol Exp Ther. 2006 July; 318(1):246-54). Four different PARs have been identified as PAR1, PAR2, PAR3 and PAR4, responding to a group of serine proteases. Modulation of PAR1-mediated signaling activities has several therapeutic applications. Interest in PAR-1 was initiated from its involvement in thrombin-induced activation of platelets. Subsequently, PAR-1 activation was found to mediate several processes in vascular biology, inflammation, malignancy, and tissue remodeling in normal development. Inhibition of PAR1 is helpful for treating thrombotic and vascular proliferative disorders as well as for inhibiting progression of cancers. PAR1 has been shown to be involved in a variety of primary human cancers including those of breast, colon, prostate, ovary and melanoma. (Zania et. al., 246-54; Wilson et. al., Cancer Res 2009, 69(7), 3188-3194; Gao et. al., Biol. Chem. 2010, 391, 803-812; Trivedi et. al., Cell 2009, 137(2), 332-343; Borensztajn et. al., Thrombosis Research 2009, 124, 219-225; Day et. al., J Thorac Cardiovasc Surg. 2006, 131, 21-7; Cunningham et. al., J. Exp. Med. 2000, 191, 455-62; Niessen et. al., Nature, 2008, 452, 654-658; Bar-Shavit et. al., US 20090215683; Perez et. al., US 20090176803; Hirano et. al., US 20100063048; Mackman et. al., US 20090022729; Teng et. al., US 20020004518).

Platelets are key mediators of thrombosis. Drugs that interfere with platelet activation substantially improve survival in arterial thrombotic disease. (Dowal et. al., Current Vascular Pharmacology, 2010, 8, 140-154). In the case of thrombus formation, the activation of platelets is initiated through the thrombin receptor pathway. The SFLLRN peptide activates platelets through PAR1. Upon activation, the platelets undergo many changes induced by multiple signaling cascades. One downstream effect of activation is the secretion of granules, which then potentiates platelet functions in controlling bleeding. Granule secretion also contributes to the growth of thrombi.

Several categories of antiplatelet agents are presently under development including those directed at platelet adhesion proteins, those directed at signaling proteins, and those directed at ligand binding sites on GPCRs. Another strategy for developing improved antiplatelet reagents directed at GPCRs is to develop drugs that act via mechanisms other than competitive antagonism at the ligand binding site. Allosteric modulators can bind GPCRs outside of the ligand binding site and induce a conformational change in the receptor. Pharmacological properties of such modulators suggest that they may have favorable therapeutic indices and increased specificity compared with competitive antagonists. In addition, reagents that target intracellular loops of GPCRs have been developed and may prove to be useful reagents for modulating GPCR signaling. (Dowal et al.).

Nishida et al. discloses morpholine compounds as factor IXa inhibitors and for the treatment of blood coagulation. (WO 2010/065717). Bauer et al. discloses a series of menthol substituted antithrombotic agents. (WO 2003/080564). Folkes et al. discloses a group of inhibitors of plasminogen activator inhibitor-1 for the treatment of thrombotic disorders. (GB 2372986, 2002). Beight et al., discloses dibenzoylbenzediamines as antithrombotic agents. (WO 1999/00127).

Jeffrey et al., discloses benzamide derivatives as allosteric modulators for the treatment of neurological and psychiatric disorders. (WO 2008/151184 A1). Zhou et al. discloses the use of a group of diaminophenyl derivatives for the treatment of pain, anxiety, depression, cocaine addiction and fragile X-syndrome. (Bioorg Med Chem Lett. 2009, 19(23): 6502-6). Platelets represent a good cellular target for pharmacological manipulation via allosteric modulation. One of the problems in developing an antiplatelet agent is achieving a potent antiplatelet effect while avoiding hemorrhagic complications. Development of allosteric modulators of platelet function could limit bleeding complications associated with many current antiplatelet agents.

SUMMARY OF THE INVENTION

The invention relates to the treatment of protease-activated receptor mediated diseases by the administration of a compound of Formula I or a prodrug or metabolite thereof:

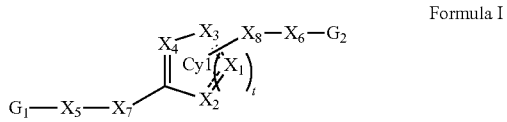

Formula I wherein,
each $X_1$, $X_2$ and $X_3$ is independently selected from absent, —[C($R_{10}$)($R_{11}$)]$_v$—, —S—, —O—, —C($R_{12}$)=C($R_{13}$)—, —C(O$R_{15}$)($R_{14}$)—, —N($R_{16}$)— and —C(O)—;
wherein v is 0, 1, 2, or 3;
each $R_{10}$, $R_{11}$, $R_{12}$, $R_{13}$, and $R_{14}$ is independently absent, hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, C(O)OH, C(O)O-alkyl, C(O)NH$_2$, C(O)N(alkyl)alkyl, C(O)N(alkyl)H, CF$_3$, CN, NO$_2$, N$_3$, sulfonyl, acyl, aliphatic, substituted aliphatic, aryl, substituted aryl, heteroaryl, substituted heteroaryl, heterocyclic or substituted heterocyclic;
Each $R_{15}$, and $R_{16}$ is independently selected from absent, hydrogen, halogen, aliphatic, substituted aliphatic, aryl or substituted aryl; alternatively two $R_{10}$, $R_{11}$, $R_{12}$, $R_{13}$, $R_{14}$, $R_{15}$ or $R_{16}$ together with the atoms to which they are attached and any intervening atoms may form an additional optionally substituted, 3, 4, 5, 6 or 7 membered ring;

$X_4$ is selected from $N(R_{15})$—, —C(O)—, —$C(OR_{16})$—, —$C(R_{10})$—, and —$C(R_{11})$=$C(R_{12})$—;

each $X_5$ and $X_6$ is independently selected from absent, —$NR_{15}$, —O— and —$CR_{16}R_{10}$;

$X_7$ is —$N(R_1)$—C(O)— or —NH—;

$X_8$ is —$N(R_2)$—C(O)— or —NH—;

Wherein each $R_1$ and $R_2$ is independently absent, hydrogen, halogen, aliphatic, substituted aliphatic, aryl or substituted aryl;

each $G_1$ and $G_2$ is selected from aliphatic, substituted aliphatic, aryl or substituted aryl, —$OR_{20}$, —$SR_{20}$, —$NR_{20}R_{21}$, —$CF_3$, —CN, —$NO_2$, —$N_3$, —$C(O)OR_{20}$, —$C(O)R_{20}$, —$C(O)NR_{20}R_{21}$, —$S(O)R_{20}$, —$S(O)NR_{20}$, —$S(O)_2R_{20}$, acyl, alkoxy, substituted alkoxy, alkylamino, substituted alkylamino, dialkylamino, substituted dialkylamino, substituted or unsubstituted alkylthio, substituted or unsubstituted alkylsulfonyl;

Wherein each $R_{20}$, and $R_{21}$ is independently selected from absent, hydrogen, halogen, aliphatic, substituted aliphatic, aryl or substituted aryl; alternatively $R_{20}$ and $R_{21}$ together with the atoms to which they are attached and any intervening atoms may form an additional optionally substituted, 3, 4, 5, 6 or 7 membered ring; and, t is 0, 1, 2 or 3.

The invention provides a method for treating PAR-mediated diseases by administration of compounds of Formula I. In one embodiment, the compounds of Formula I inhibit platelet activation.

DETAILED DESCRIPTION OF THE INVENTION

Figure 1:
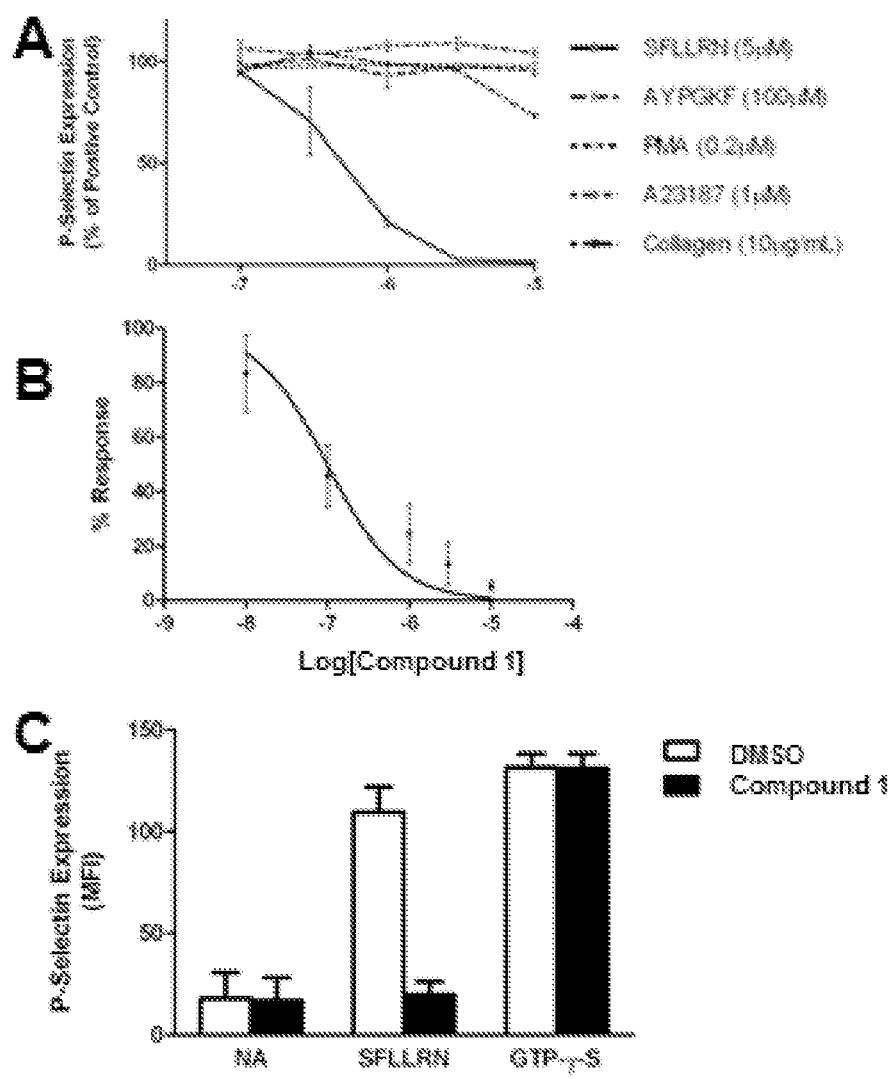
FIG. 1: (A) Compound-1 inhibits platelet activation induced through PAR1 selectively without inhibiting activation through PAR4; (B) Compound-1 inhibits PAR1 induced activation of HEK293 cells transfected with rPAR1; (C) Compound-1 inhibits PAR1 mediated, but not GTP-γ-S mediated platelet activation in permeabilized platelets.

The invention relates to the treatment of Protease-activated receptor mediated diseases by the administration of a compound of formula I or a prodrug or metabolite thereof:

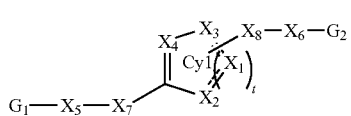

Formula I wherein, each $X_1$, $X_2$ and $X_3$ is independently selected from absent, —[$C(R_{10})(R_{11})$]$_v$—, —S—, —O—$C(R_{12})$=$C(R_{13})$—, —$C(OR_{15})(R_{14})$—, —$N(R_{16})$— and —C(O)—;

wherein v is 0, 1, 2, or 3;

each $R_{10}$, $R_{11}$, $R_{12}$, $R_{13}$, and $R_{14}$ is independently absent, hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, C(O)OH, C(O)O-alkyl, C(O)NH$_2$, C(O)N(alkyl)alkyl, C(O)N(alkyl)H, CF$_3$, CN, NO$_2$, N$_3$, sulfonyl, acyl, aliphatic, substituted aliphatic, aryl, substituted aryl, heteroaryl, substituted heteroaryl, heterocyclic or substituted heterocyclic;

Each $R_{15}$, and $R_{16}$ is independently selected from absent, hydrogen, halogen, aliphatic, substituted aliphatic, aryl or substituted aryl; alternatively two $R_{10}$, $R_{11}$, $R_{12}$, $R_{13}$, $R_{14}$, $R_{15}$ or $R_{16}$ together with the atoms to which they are attached and any intervening atoms may form an additional optionally substituted, 3, 4, 5, 6 or 7 membered ring;

$X_4$ is selected from $N(R_{15})$—, —C(O)—, —$C(OR_{16})$—, —$C(R_{10})$—, and —$C(R_{11})$=$C(R_{12})$—;

each $X_5$ and $X_6$ is independently selected from absent, —$NR_{15}$, and —$CR_{16}R_{10}$;

$X_7$ is —$N(R_1)$—C(O)— or —NH—;

$X_8$ is —$N(R_2)$—C(O)— or —NH—;

Wherein each $R_1$ and $R_2$ is independently absent, hydrogen, halogen, aliphatic, substituted aliphatic, aryl or substituted aryl;

each $G_1$ and $G_2$ is selected from aliphatic, substituted aliphatic, aryl or substituted aryl —$OR_{20}$, —$SR_{20}$, —$NR_{20}R_{21}$, —$CF_3$, —CN, —$NO_2$, —$N_3$, —$C(O)OR_{20}$, —$C(O)R_{20}$, —$C(O)NR_{20}R_{21}$, —$S(O)R_{20}$, —$S(O)NR_{20}$, —$S(O)_2R_{20}$, acyl, alkoxy, substituted alkoxy, alkylamino, substituted alkylamino, dialkylamino, substituted dialkylamino, substituted or unsubstituted alkylthio, substituted or unsubstituted alkylsulfonyl;

Wherein each $R_{20}$, and $R_{21}$ is independently selected from absent, hydrogen, halogen, aliphatic, substituted aliphatic, aryl or substituted aryl; alternatively $R_{20}$ and $R_{21}$ together with the atoms to which they are attached and any intervening atoms may form an additional optionally substituted, 3, 4, 5, 6 or 7 membered ring; and, t is 0, 1, 2 or 3.

In one embodiment, the invention relates to the treatment of Protease-activated receptor mediated diseases by the administration of a compound of Formula II or a prodrug or metabolite thereof:

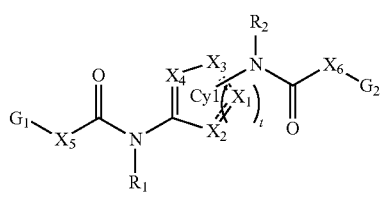

Formula II wherein, each $R_1$ and $R_2$ is independently absent, hydrogen, halogen, aliphatic, substituted aliphatic, aryl or substituted aryl;

each $X_1$, $X_2$ and $X_3$ is independently selected from absent, $-[C(R_{10})(R_{11})]_v-$, $-S-$, $-O-$, $C(R_{12})=C(R_{13})-$, $-C(OR_{15})(R_{14})-$, $-N(R_{16})-$ and $-C(O)-$;

wherein v is 0, 1, 2, or 3;

each $R_{10}$, $R_{11}$, $R_{12}$, $R_{13}$, and $R_{14}$ is independently absent, hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, C(O)OH, C(O)O-alkyl, C(O)NH$_2$, C(O)N(alkyl)alkyl, C(O)N(alkyl)H, CF$_3$, CN, NO$_2$, N$_3$, sulfonyl, acyl, aliphatic, substituted aliphatic, aryl, substituted aryl, heteroaryl, substituted heteroaryl, heterocyclic or substituted heterocyclic;

Each $R_{15}$, and $R_{16}$ is independently selected from hydrogen, halogen, aliphatic, substituted aliphatic, aryl or substituted aryl; alternatively two $R_{10}$, $R_{11}$, $R_{12}$, $R_{13}$, $R_{14}$, $R_{15}$ or $R_{16}$ together with the atoms to which they are attached and any intervening atoms may form an additional optionally substituted, 3, 4, 5, 6 or 7 membered ring;

$X_4$ is selected from $N(R_{15})-$, $-C(O)-$, $-C(OR_{16})-$, $-C(R_{10})-$, and $-C(R_{11})=C(R_{12})-$;

each $X_5$ and $X_6$ is independently selected from absent, $-NR_{15}$, $-O-$ and $-CR_{16}R_{10}$;

each $G_1$ and $G_2$ is selected from aliphatic, substituted aliphatic, aryl or substituted aryl; and t is 0, 1, 2 or 3.

In a preferred embodiment Cy1 and $G_2$ are aromatic groups and $G_1$ is an alkyl group.

In a preferred embodiment, the invention provides a method for the treatment of PAR-mediated diseases by administration of a compound of Formula III:

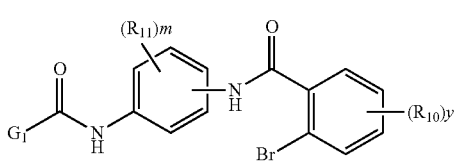

Formula III wherein $G_1$, and $R_{10}$ are as defined above; and
Each m and y is independently selected from 0, 1, 2, 3 or 4.

In a preferred embodiment, the invention provides a method for the treatment of PAR-mediated diseases by administration of a compound of Formula IIIA:

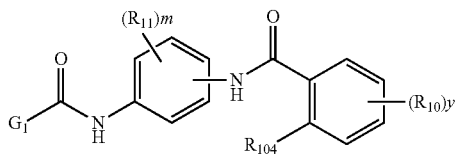

Formula IIIA

Wherein $R_{104}$ is a halogen, Alkyl, $-$OAlkyl, $-$SAlkyl; preferably, $-$OCH$_3$, $-$OCH$_2$CH$_3$, $-$CH$_3$, $-$CH$_2$CH$_3$.

In one embodiment, the invention provides a method for the treatment of PAR-mediated diseases by administration of a compound of Formula IV, V or VI:

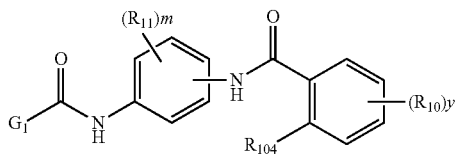

Formula IV

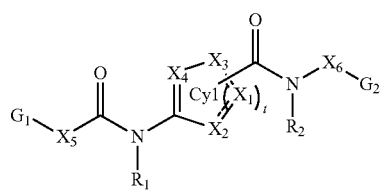

Formula V

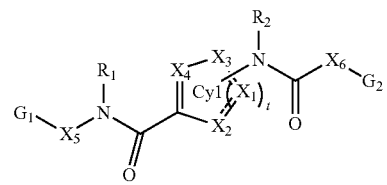

Formula VI

In a preferred embodiment, the invention provides a method for the treatment of PAR-mediated diseases by administration of a compound of Formula VII:

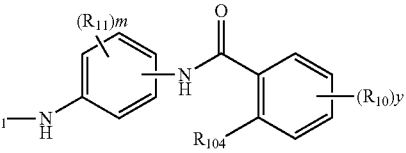

Formula VII

In a more preferred embodiment, $G_1$ is selected from C$_2$-C$_{10}$ alkyl, C$_2$-C$_{10}$ flourinated alkyl; preferably, isobutyl, ethyl, propyl, isopropyl, n-butyl, tert-butyl, n-pentyl, neopentyl, n-hexyl, cyclopropyl, cyclobutyl, cyclopentyl or cyclohexy; more preferably, isobutyl.

In a preferred embodiment, ring Cy1 is selected from:
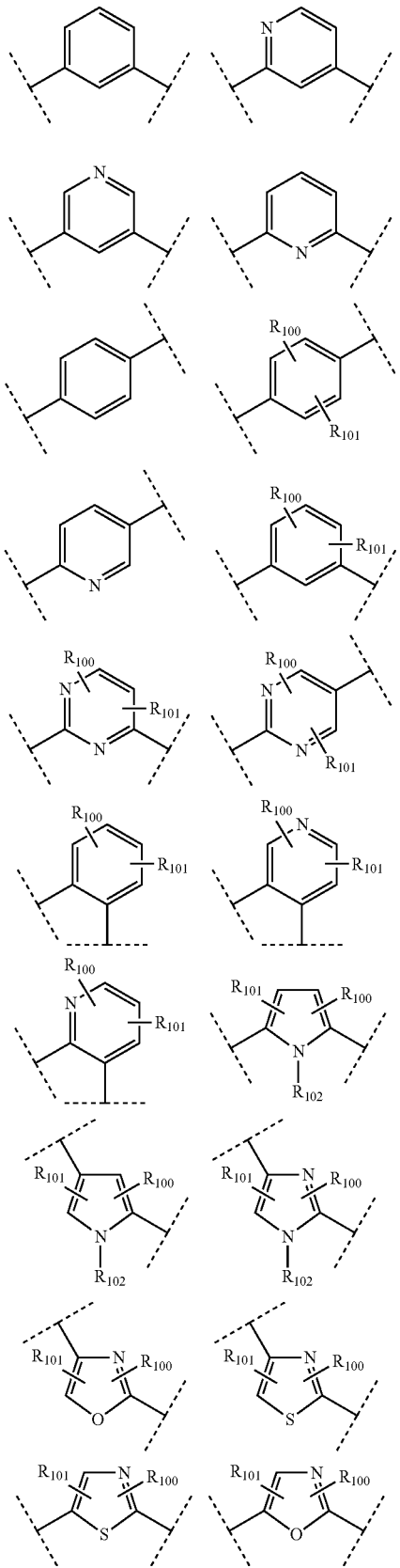
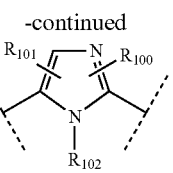
wherein each $R_{100}$, $R_{101}$ and $R_{102}$ is selected from hydrogen, $C_1$-$C_8$ alkyl, $C_2$-$C_8$ alkenyl, $C_2$-$C_8$ alkynyl and $C_3$-$C_8$ cycloalkyl.
In a preferred embodiment, $G_1$ is selected from:
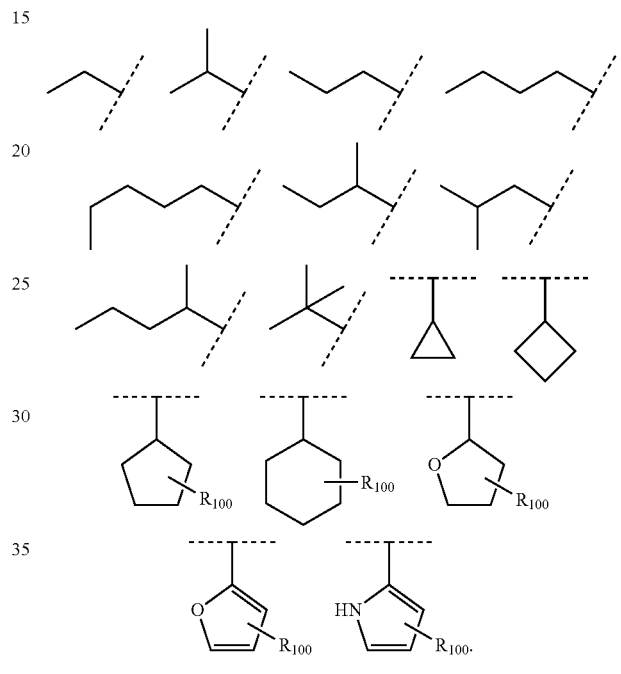
In a preferred embodiment, ring $G_2$ is selected from:
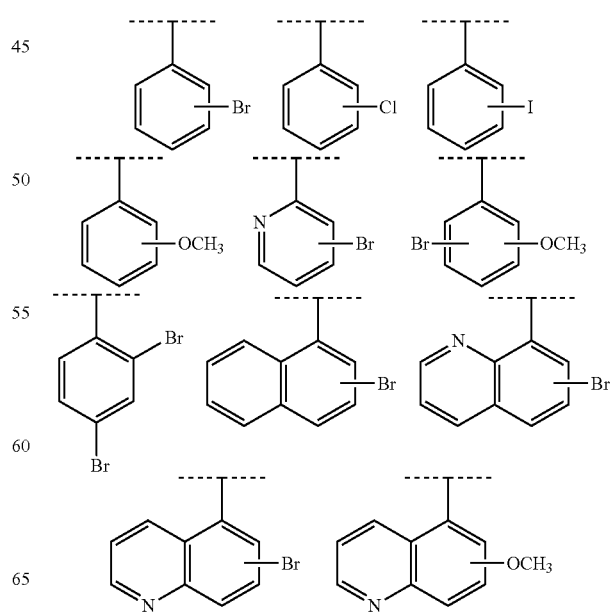

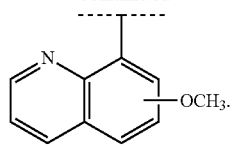
In a more preferred embodiment, a compound of Formula I or II is selected from Table A:
TABLE A
| # | Structure |
|---|---|
| 1 | 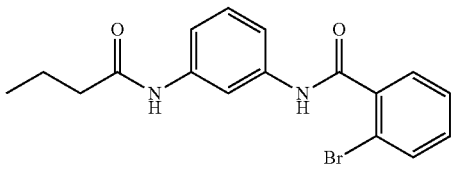 |
| 2 | 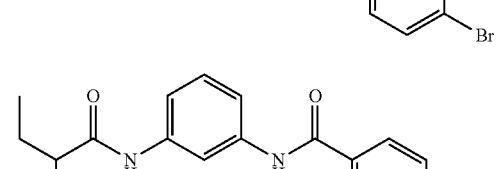 |
| 3 | 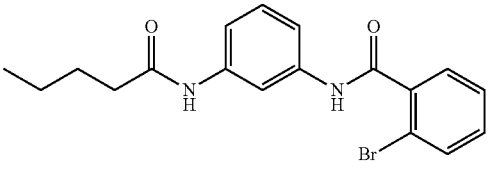 [SMILES: CCCCC(=O)Nc1cccc(NC(=O)c2ccccc2Br)c1] |
| 4 | 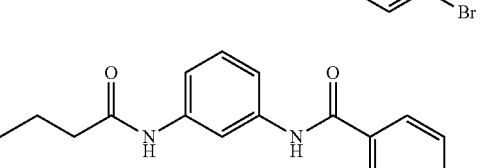 |
| 5 | 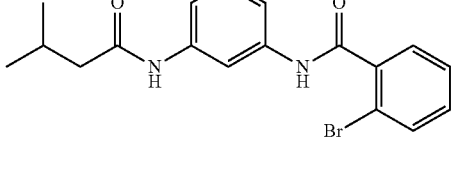 |
| 6 | 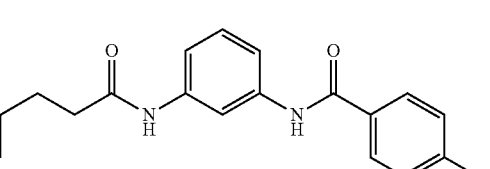 |
| 7 | 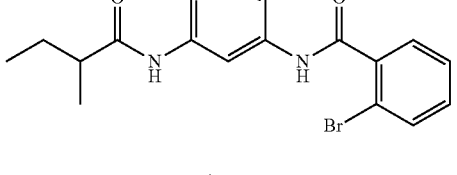 |
TABLE A-continued
| # | Structure |
|---|---|
| 8 | 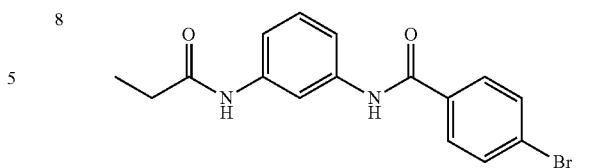 |
| 9 | 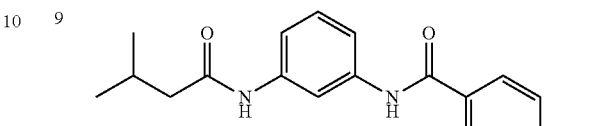 |
| 10 | 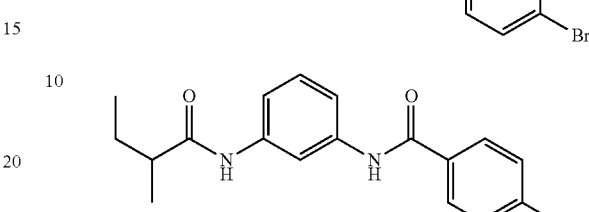 |
| 11 | 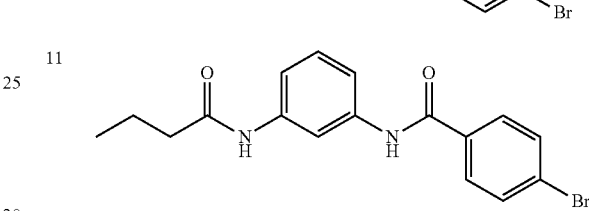 |
| 12 | 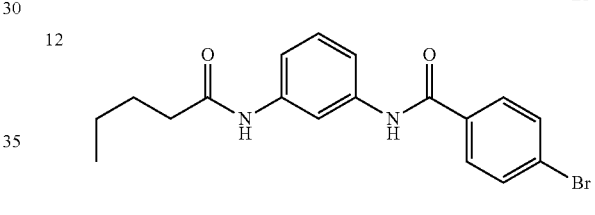 |
| 13 | 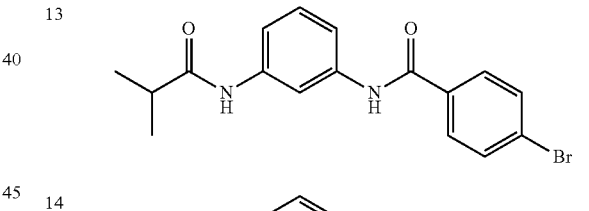 |
| 14 | 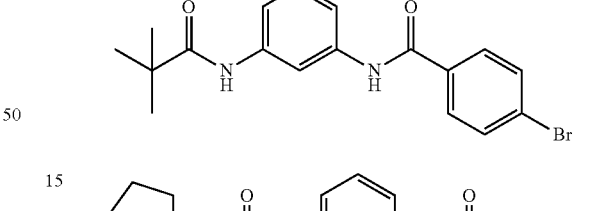 |
| 15 | 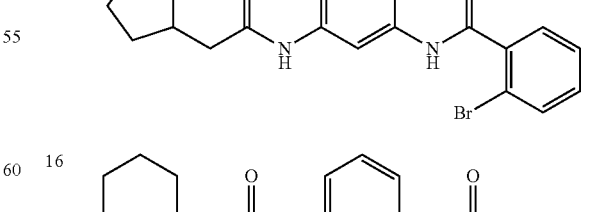 |
| 16 | 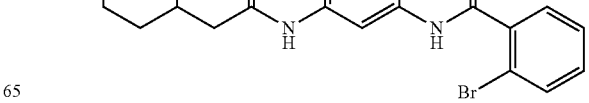 |

TABLE A-continued
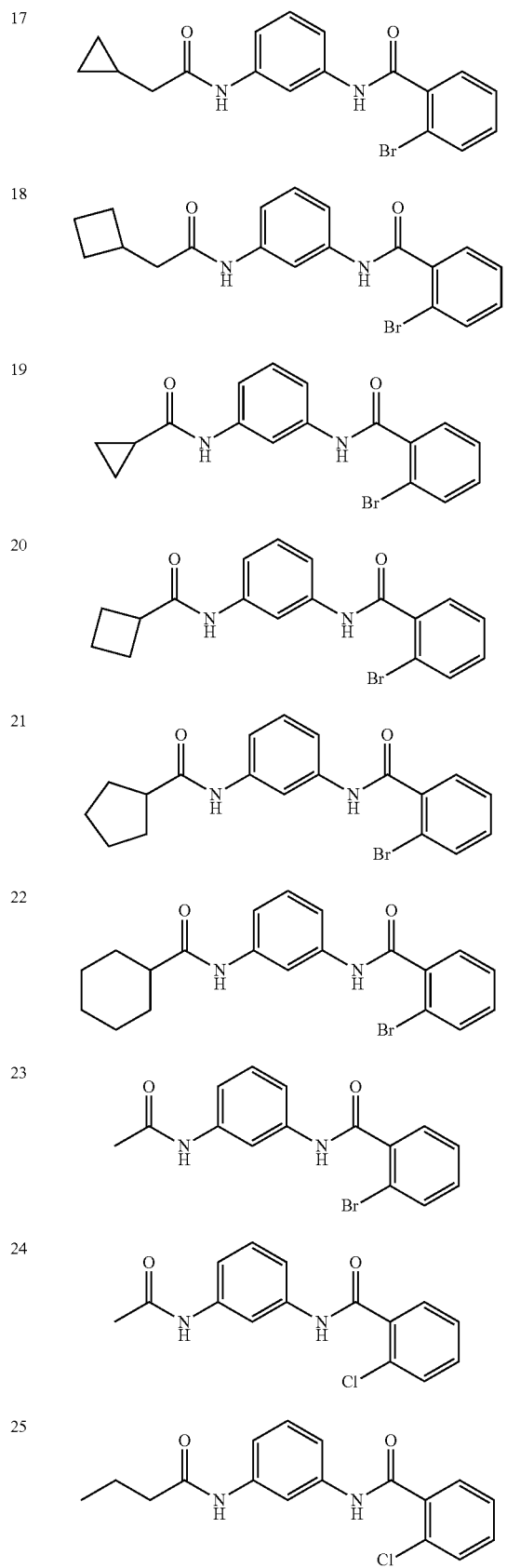
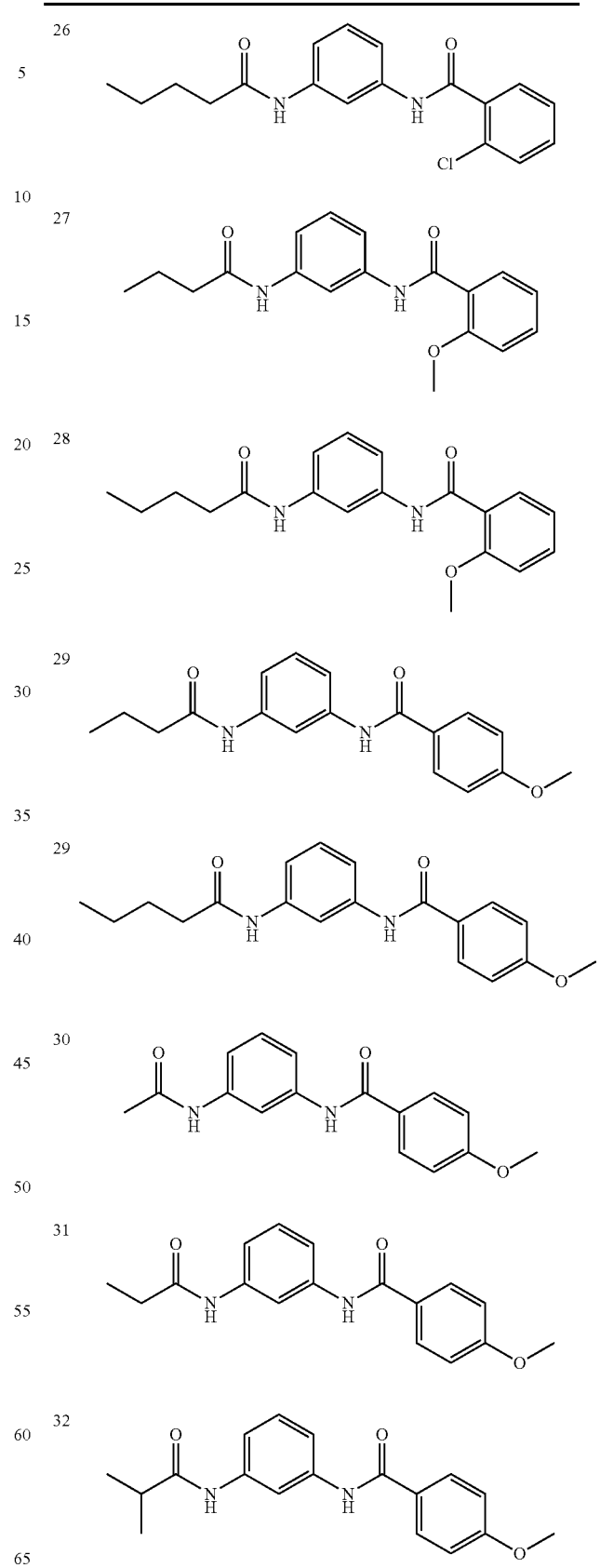

TABLE A-continued
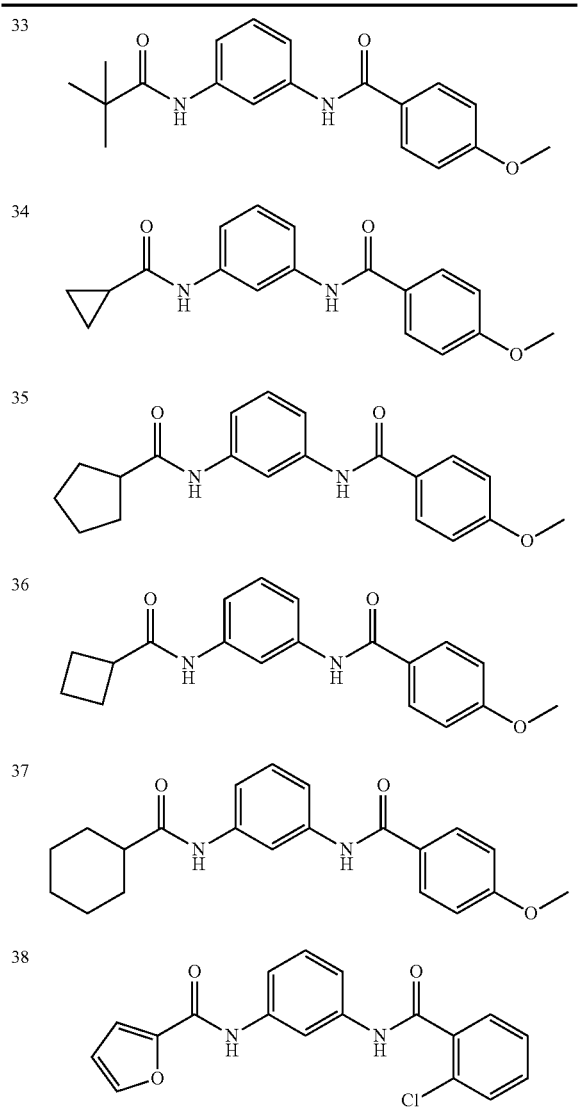
TABLE A-continued
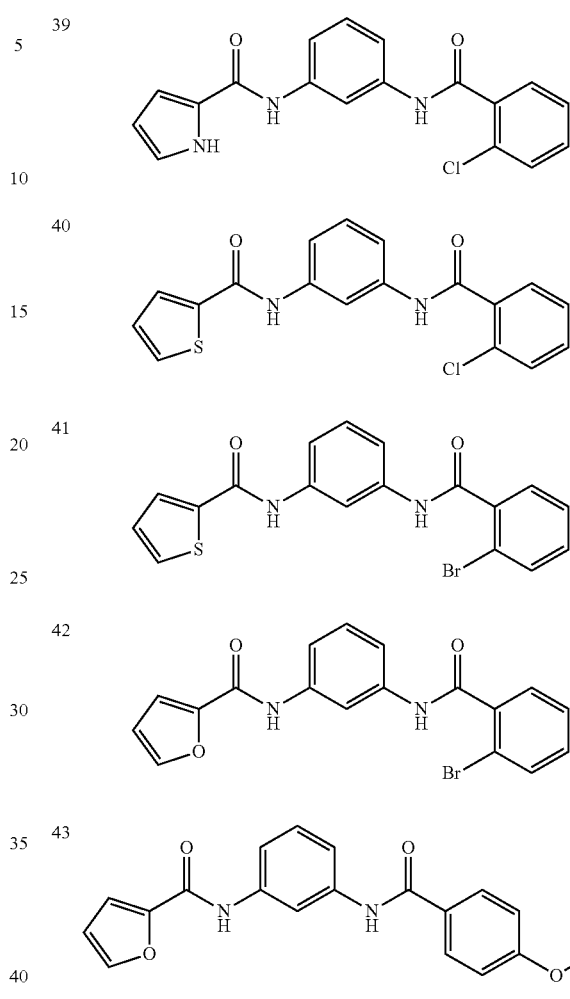
In a preferred embodiment, a compound of Formula I is selected from Table B:
TABLE B
| Compound |
|---|
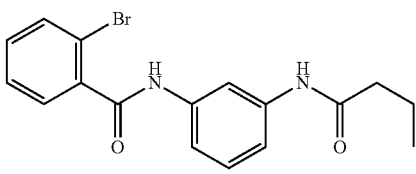 [SMILES: CCCC(=O)Nc1cccc(NC(=O)c2ccccc2Br)c1]
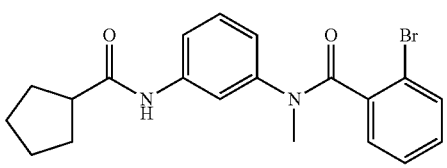 [SMILES: CN(C(=O)c1ccccc1Br)c1cccc(NC(=O)C2CCCC2)c1]
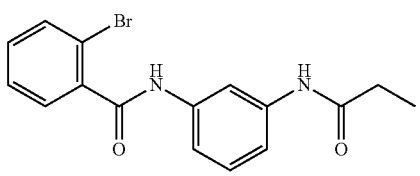 [SMILES: CCC(=O)Nc1cccc(NC(=O)c2ccccc2Br)c1]
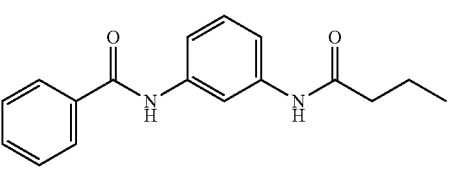 [SMILES: CCCC(=O)Nc1cccc(NC(=O)c2ccccc2)c1]

TABLE B-continued
| Compound | |
|---|---|
| 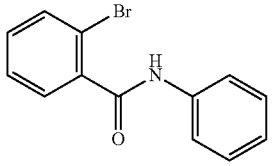 [SMILES: O=C(Nc1ccccc1)c1ccccc1Br] | 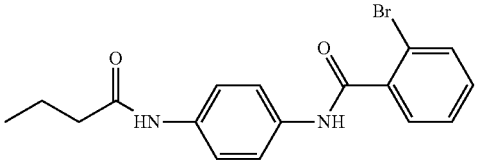 [SMILES: CCCC(=O)Nc1ccc(NC(=O)c2ccccc2Br)cc1] |
| 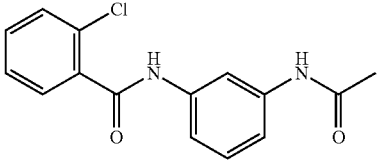 [SMILES: CC(=O)Nc1cccc(NC(=O)c2ccccc2Cl)c1] | 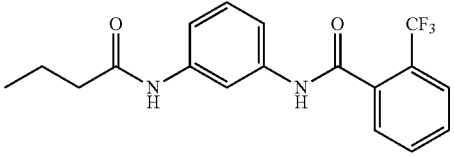 [SMILES: CCCC(=O)Nc1cccc(NC(=O)c2ccccc2C(F)(F)F)c1] |
| 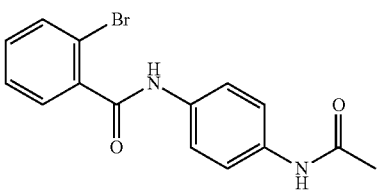 [SMILES: CC(=O)Nc1ccc(NC(=O)c2ccccc2Br)cc1] | 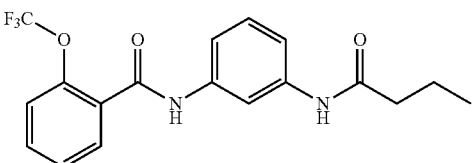 |
| 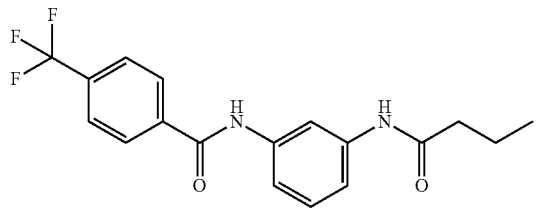 [SMILES: CCCC(=O)Nc1cccc(NC(=O)c2ccc(C(F)(F)F)cc2)c1] | 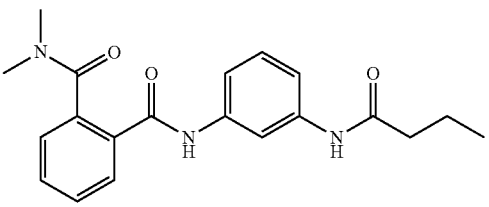 [SMILES: CCCC(=O)Nc1cccc(NC(=O)c2ccccc2C(=O)N(C)C)c1] |
|  | 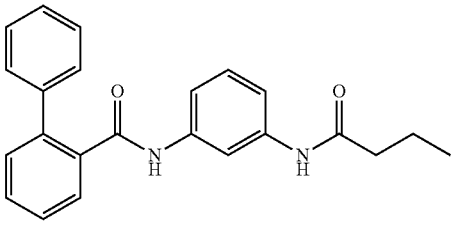 [SMILES: CCCC(=O)Nc1cccc(NC(=O)c2ccccc2-c2ccccc2)c1] |
| 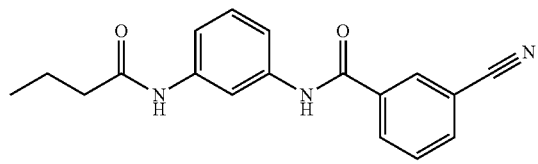 [SMILES: CCCC(=O)Nc1cccc(NC(=O)c2cccc(C#N)c2)c1] | 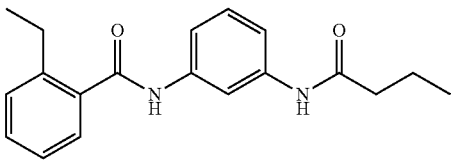 [SMILES: CCCC(=O)Nc1cccc(NC(=O)c2ccccc2CC)c1] |
| 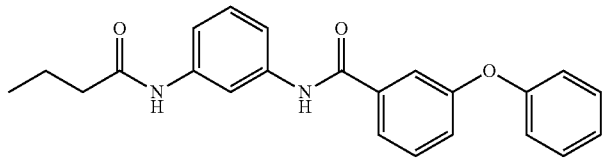 [SMILES: CCCC(=O)Nc1cccc(NC(=O)c2cccc(Oc3ccccc3)c2)c1] | 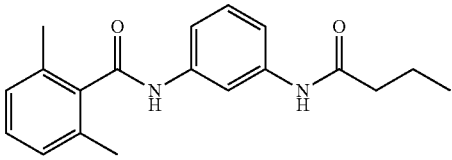 [SMILES: CCCC(=O)Nc1cccc(NC(=O)c2c(C)cccc2C)c1] |
| 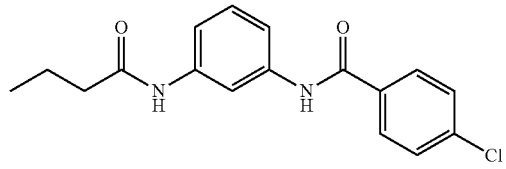 [SMILES: CCCC(=O)Nc1cccc(NC(=O)c2ccc(Cl)cc2)c1] | 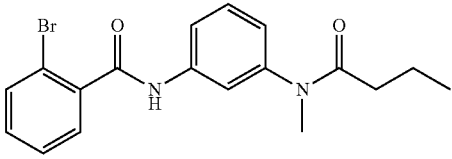 [SMILES: CCCC(=O)N(C)c1cccc(NC(=O)c2ccccc2Br)c1] |

TABLE B-continued

Compound

TABLE B-continued
Compound
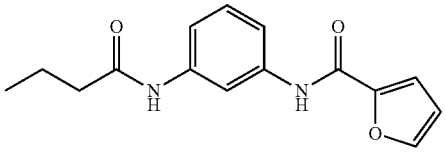 [SMILES: CCCC(=O)Nc1cccc(NC(=O)c2ccco2)c1]

TABLE B-continued

Compound

[Chemical structures shown]

In a preferred embodiment, a compound of Formula I or II is selected from Table C:

TABLE C

[Structures numbered 1-10 shown]

TABLE C-continued

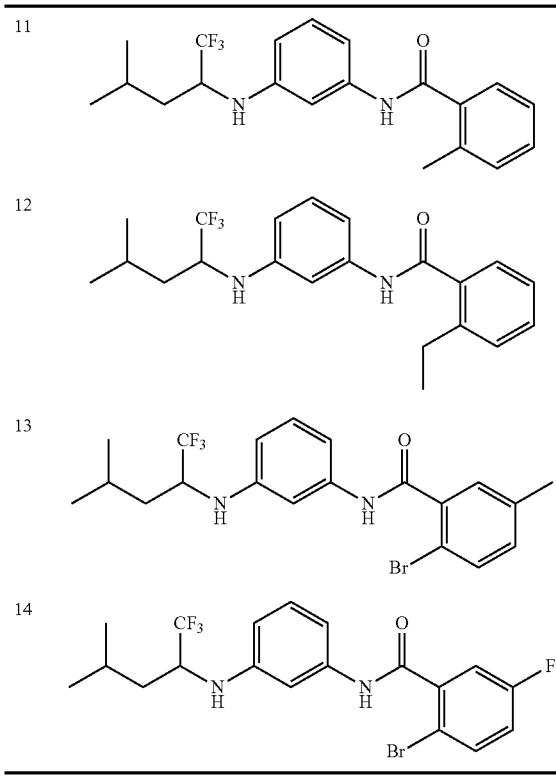

Wherein each $R_{105}$ is selected from $C_1$-$C_{10}$ alkyl and $C_3$-$C_{10}$ cyclo alkyl, preferably methyl, ethyl, propyl, isopropyl, butyl, isobutyl, tert-butyl, cyclopropyl, cyclobutyl, cyclopentyl and cyclohexyl.

Each $R_{106}$ is selected from Br, F, I, Cl, methyl, ethyl, propyl, isopropyl, butyl, isobutyl, tert-butyl, —$OCH_3$, —$OCF_3$ and —$OCH_2CH_3$.

The invention provides methods for reducing platelet activation, reducing platelet aggregation and reducing thrombosis. The invention further provides methods of treating or preventing diseases or disorders in which the pathology of the disease or disorder involves one or more of platelet activation, platelet aggregation and thrombus formation.

The invention encompasses a method of reducing platelet activation, platelet aggregation or thrombosis, the method comprising administering an effective amount of a compound of Formula I or a pharmaceutically acceptable salt thereof, such that platelet activation, aggregation or thrombosis is reduced.

In another embodiment, the disease or disorder is selected from the group consisting of: acute myocardial infarction; stable angina; unstable angina; transient ischemic attack; cerebrovascular disease; peripheral vascular disease; placental insufficiency; thrombosis subsequent to or associated with a surgical procedure; thrombosis associated with atrial fibrillation; and inflammation. In a preferred embodiment, the inflammation is inflammation associated with wound healing, atherosclerosis or allergy. In another embodiment, the surgical procedure is selected from the group consisting of: aortocoronary bypass surgery; coronary angioplasty; stent placement; and insertion of prosthetic heart valves.

The invention further encompasses a pharmaceutical composition comprising a compound of Formula I or II and a second agent selected from the group consisting of: aspirin, ticlopidine, clopidrogel, Abiximab, c7E3 Fab, Tirofiban, Eptifibatide, an anti-GPIIbIIIa agent, and a phosphodiesterase inhibitor.

In one embodiment, the present invention a method for inhibiting platelet activation, comprising administering a compound of Formula I or II.

The present invention also provides methods of inhibiting thrombus formation in a mammal, comprising administering to said mammal a composition comprising a compound of Formula I or II.

In one embodiment, the invention provides a therapeutic method for treating or preventing proliferative diseases, in particular proliferative diseases of endothelial cells, fibroblasts, nephrocytes, osteosarcoma cells, muscle cells, cancer cells and/or glia cells, or malignancies such as cancer of the breast, lung, brain, kidney, skin, prostate, ovary or colon, comprising administering to a patient suffering from the disease, comprising administering to a patient suffering from the disease, a therapeutically effective dose of a compound of Formula I or II.

In another embodiment, a composition comprising an allosteric modulator of GPCR selected from a compound of Formula I or II is administered in combination with a competitive antagonist of GPCR. In a preferred embodiment, a combination of a PAR1 allosteric modulator of Formula I and a competitive antagonist of PAR1 is disclosed.

Without being bound to any theory it is postulated that the compounds of the current invention act as inhibitors of GPCR signaling where they target the proximal cell-surface receptors. This allows for the selective inhibition of GPCR activation and signaling, which are considered part of the proximal signaling events involved in platelet activation. Furthermore, the compounds of Formula I may act as allosteric inhibitors of GPCR activation and signaling. As such, it is postulated that the compounds of Formula I or II bind at a site separate from the ligand binding site and induce a conformational change in the receptor.

The invention further relates to inhibiting or reducing PAR1-mediated signaling and/or thrombus formation via a non-orthosteric mechanism and inhibits both platelet accumulation and fibrin generation that occurs during thrombus formation at sites of vascular injury. Without being bound to any particular theory, it is postulated that at least some of the compounds of Formula I-VI inhibit PAR1 activity via a non-orthosteric mechanism.

The invention further relates to a method of treating a vascular disorder associated with increased PAR-1 by administering a compound of Formula I-VI to a subject in need thereof. The increased level of PAR-1 can be determined by any number of methods readily available to one skilled in the art, for example by evaluating Protease ActivatedReceptor (PAR)-1 levels.

The invention further relates to a method of selectively inhibiting PAR-1 related disease wherein PAR-4 activity is not significantly inhibited by bringing a compound of Formula I-VI PAR-1. In a preferred embodiment the selectivity of inhibition for PAR-1 over PAR-4 is between about 2 to about 10,000; preferably between about 5 and 100, more preferably between about 10 and 1,000. The selectivity for inhibition can be determined by determining the $IC_{50}$ value of inhibition for PAR-1 and PAR-4. The ratio of $IC_{50}$ values ($IC_{50}$ for PAR-4/$IC_{50}$ for PAR-4) is considered the selectivity where $IC_{50}$ is determined using the method described below.

The invention further relates to a method of treating an inflammatory state involving atherosclerotic disease, allergic inflammation, asthma, inflammation accompanying wound healing, or inflammation accompanying autoimmune disease such as in rheumatoid arthritis, comprising administering to a patient suffering from the disease, a therapeutically effective dose of a compound of Formula I-VI or a compound from Table A or B.

DEFINITIONS

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include branched, straight chain and cyclic, substituted or unsubstituted saturated aliphatic hydrocarbon radicals/groups having the specified number of carbons. Preferred alkyl groups comprise about 1 to about 24 carbon atoms ("$C_1$-$C_{24}$") preferably about 7 to about 24 carbon atoms ("$C_7$-$C_{24}$"), preferably about 8 to about 24 carbon atoms ("$C_8$-$C_{24}$"), preferably about 9 to about 24 carbon atoms ("$C_9$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$") preferably about 7 to about 24 carbon atoms ("$C_7$-$C_{24}$"), preferably about 8 to about 24 carbon atoms ("$C_8$-$C_{24}$"), and preferably about 9 to about 24 carbon atoms ("$C_9$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" and "drug" as used herein all include pharmaceutically acceptable salts, co-crystals, solvates, hydrates, polymorphs, enantiomers, diastereoisomers, racemates and the like of the compounds and drugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semisolid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha- (α), beta- (β) and gamma- (γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect).

In certain embodiments, one or more therapeutic agents of the dosage unit may exist in an extended or control release formulation and additional therapeutic agents may not exist in extended release formulation. In one embodiment, the extended release contemplates the substantially continuous delivery of drug over an extended period of time, such as greater than one, two, three, four or more weeks. For example, an agent described herein may exist in a controlled release formulation or extended release formulation in the same dosage unit with another agent that may or may not be in either a controlled release or extended release formulation. Thus, in certain embodiments, it may be desirable to provide for the immediate release of one or more of the agents described herein, and the controlled release of one or more other agents. The rate of delivery may be altered, for example, by varying the lactide/glycolide ratio in a poly(D, L-lactide-co-glycolide) encapsulation. Other polymers that may be used include polyacetal polymers, polyorthoesters, polyesteramides, polycaprolactone and copolymers thereof, polycarbonates, polyhydroxybuterate and copolymers thereof, polymaleamides, copolyaxalates and polysaccharides. In one embodiment of the invention, a compound of Formula I is formulated with an extended release component, such as a coated extended release matrix, an extended release matrix, or an extended release bead matrix. In one example, a compound of Formula I is used in combination with a polymer matrix (e.g., Eudragit), Hydroxypropyl methyl cellulose (HPMC) and/or a polymer coating (e.g., Eudragit). Such formulations can, for example, be compressed into solid tablets or granules or formed into pellets for capsules or tablets. Extended release oral formulation can be prepared using additional methods known in the art. For example, a suitable extended release form of a compound of Formula I may be a matrix tablet composition. Suitable matrix forming materials include, for example, waxes (e.g., carnauba, bees wax, paraffin wax, ceresine, shellac wax, fatty acids, and fatty alcohols), oils, hardened oils or fats (e.g., hardened rapeseed oil, castor oil, beef tallow, palm dil, and soya bean oil), and polymers (e.g., hydroxypropyl cellulose, polyvinylpyrrolidone, hydroxypropyl methyl cellulose, and polyethylene glycol). Other suitable matrix tabletting materials are microcrystalline cellulose, powdered cellulose, hydroxypropyl cellulose, ethyl cellulose, with other carriers, and fillers. Tablets may also contain granulates, coated powders, or pellets. Tablets may also be multi-layered. Multi-layered tablets are especially preferred when the active ingredients have markedly different pharmacokinetic profiles. Extended release formulations can be made by spray drying polymer-drug mixtures, emulsion-based technologies, coacervation based technologies, film casting, extrusion based technologies and other processes to manufacture polymer-drug microparticles possessing an extended release profile. Examples of suitable extended release technologies that can be used to incorporate the compounds of Formula I described herein include, without limitation, the MEDISORB® technology, as described in, for example, U.S. Pat. No. 6,264,987 to Wright, U.S. Pat. No. 5,654,008 and/or U.S. Pat. No. 5,792,477, for example; the PROLEASE® technology, as described, for example in U.S. Pat. No. 6,358,443 to Herbert; the technologies described by Southern Research Institute, as described for example in U.S. Pat. No. 6,306,425; and "Method of Preparing Sustained Release Microparticles," U.S. Application No. 60/441,946, filed Jan. 23, 2003, and the technologies described by Alza Corp., including the ALZAMER® Depot injection technology. The contents of these patents are incorporated herein by reference in their entirety.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

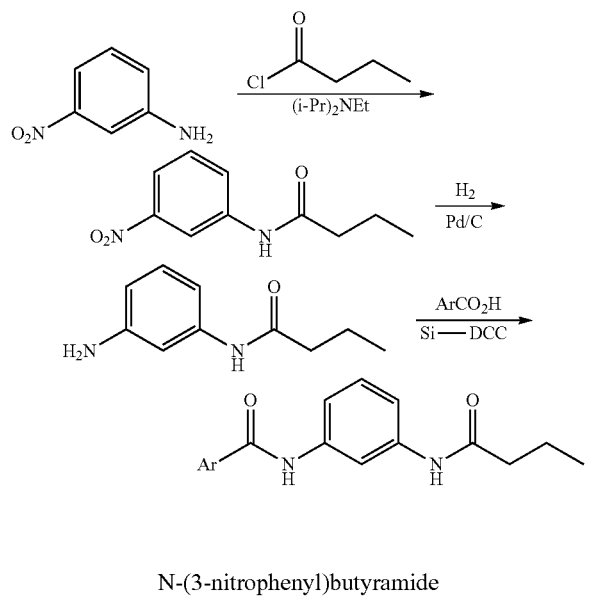

N-(3-nitrophenyl)butyramide

3-Nitroaniline (6.00 g, 43.4 mmol) was sealed in a flask with stir bar under nitrogen and dissolved with dichloromethane (DCM, 145 mL). The solution was cooled on ice before (i-Pr)$_2$NEt (8.35 ml, 47.8 mmol) and butyryl chloride (5.00 ml, 47.8 mmol) were added. The flask was removed from the ice and stirred for 16 h. The reaction was then diluted with DCM and aq. 1 M HCl, the layers were separated, and the combined organics were washed again with 1 M aq. HCl, then twice with half-saturated aq. NaHCO$_3$, then brine. The organic phase was dried over MgSO$_4$, filtered, and concentrated, yielding a yellow oil (9.04 g, 100%). LRMS (ESI−) (M−H): 207.06. The crude oil was used without further purification in the subsequent reaction.

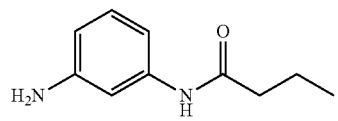

N-(3-aminophenyl)butyramide

A solution of N-(3-nitrophenyl)butyramide (8.60 g, 41.3 mmol) in MeOH (207 mL) was divided between two 500 mL flasks with stir bars. Each flask was flushed well with nitrogen, then 5% palladium on carbon (4.40 g, 2.065 mmol) was added, half to each flask. A 3-way adapter with a large hydrogen-filled balloon was attached to each flask, and the reactions were evacuated and back-filled with hydrogen five times, while stirring vigorously. The reactions were then stirred for 16 h, then filtered through a funnel packed with Celite. The filter cake was washed with MeOH, and the filtrate was concentrated, redissolved with DCM, then purified by column chromatography (EtOAc/hexanes gradient) to yield a white solid after precipitating from hexanes (5.87 g, 80%). LRMS (ESI+) (M+H): 179.18.

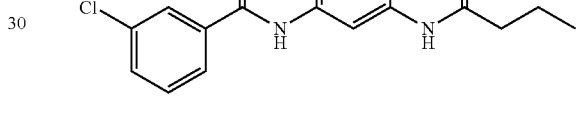

N-(3-butyramidophenyl)-3-chlorobenzamide

N-(3-Aminophenyl)butyramide (30 mg, 0.168 mmol), 3-chlorobenzoic acid (39.5 mg, 0.252 mmol), HOBt (28.4 mg, 0.185 mmol), and silica-supported DCC (from Silicycle Inc., 362 mg, 0.337 mmol) were added to a 13×100 mm test tube with stir bar. The tube was sealed with a rubber septum and dry DCM (3 mL) was added, then the reaction was stirred for 15 h. 50% CH$_3$CN/DCM (4 mL) was then added, followed by silica-supported trimethylammonium carbonate (from Silicycle Inc., 534 mg, 0.337 mmol). The mixture was stirred for 1 h, then filtered through Celite and washed with 50% CH$_3$CN/DCM (4 mL) and concentrated. The crude solid was redissolved with DCM and purified by column chromatography (EtOAc/hexanes gradient) to yield a white solid after precipitating from hexanes (39 mg, 73%). LRMS (ESI+) (M+H): 317.22.

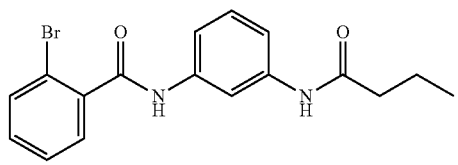 [SMILES: CCCC(=O)Nc1cccc(NC(=O)c2ccccc2Br)c1]

2-bromo-N-(3-butyramidophenyl)benzamide

2-Bromobenzoic acid (259 mg, 1.29 mmol) was sealed in a flask with stir bar under nitrogen, then dissolved with dichloromethane (7.5 mL) and cooled on ice. Oxalyl chloride (113 μL, 1.29 mmol) and N,N-dimethylformamide (4 μL, 0.06 mmol) were added, then the reaction was removed from the ice bath and stirred for 3 h with a vent to an oil bubbler. N-(3-Aminophenyl)butyramide (200 mg, 1.12 mmol) was then added, followed by pyridine (209 μL, 2.58 mmol). After 18 h, LC-MS analysis showed complete consumption of the amine reactant. The reaction was diluted with ethyl acetate (40 mL) and 1 M aqueous HCl (40 mL), then the layers were separated and the organic phase was washed again with aqueous HCl, then twice with half-saturated aqueous NaHCO$_3$, then brine. The organics were dried over Na$_2$SO$_4$, filtered, and concentrated to a colorless oil. The oil was redissolved with dichloromethane, then hexane was added to induce the precipitation of an amorphous solid. The suspension was concentrated and dried under hi-vacuum to yield the title compound (382 mg, 94%). LRMS (ESI+) (M+H): 361.12.

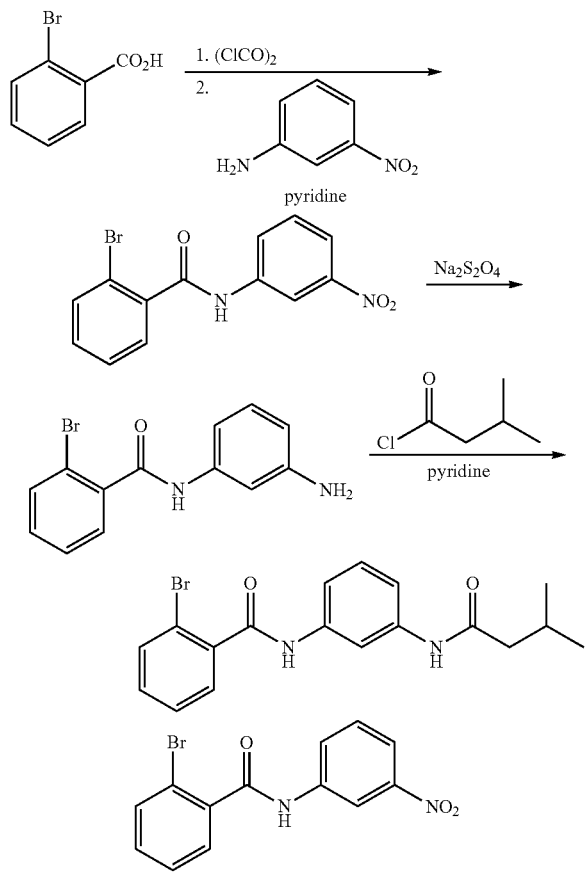

2-bromo-N-(3-nitrophenyl)benzamide

2-Bromobenzoic acid (5.02 g, 25.0 mmol) was sealed in a 250 mL flask with stir bar under nitrogen. Dichloromethane (72 mL) was then added and the solution was cooled on ice. Oxalyl chloride (2.19 ml, 25.0 mmol) and N,N-dimethylformamide (17 μL, 0.22 mmol) were added, and the reaction was removed from the ice bath and the resulting suspension was stirred for 20 h with a vent to an oil bubbler. After this time, the pale yellow solution was cooled on ice, then pyridine (4.04 ml, 50.0 mmol) and 3-nitroaniline (3.00 g, 21.7 mmol) were added. The reaction was then removed from the ice bath, and a water condenser was attached to the flask. The reaction was heated in an oil bath at 45° C., and after 1 h LC-MS analysis showed the reaction to be complete. The reaction was diluted with ethyl acetate (250 mL) and 1 M aqueous HCl (100 mL), then the layers were separated and the organic phase was washed again with aqueous HCl, then twice with half-saturated aqueous NaHCO$_3$, then brine. The organics were dried over Na$_2$SO$_4$, filtered, and concentrated to a yellow solid, which was dried and pulverized several times, yielding the title compound (6.89 g, 99%). LRMS (ESI+) (M+H): 321.01.

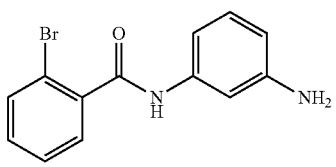 [SMILES: Nc1cccc(NC(=O)c2ccccc2Br)c1]

N-(3-aminophenyl)-2-bromobenzamide

2-Bromo-N-(3-nitrophenyl)benzamide (6.89 g, 21.5 mmol) was added to a 1 L flask with stir bar and dissolved with THF (143 mL). Sodium dithionite (37.4 g, 215 mmol) (aka sodium hydrosulfite) was added to a separate flask and dissolved with water (143 mL). The resulting cloudy solution was added to the solution of substrate, and the flask was sealed and flushed with nitrogen, then stirred vigorously for 16 h with a vent line to an oil bubbler. After this time LC-MS analysis showed complete conversion to a mixture of the desired product plus its N-sulfate. To hydrolyze the sulfated material, saturated aqueous ammonium chloride (30 mL) was added, and the mixture was refluxed for 4 h. The layers were then separated, and the aqueous layer was extracted twice with ethyl acetate. The combined organics were washed with brine, then dried over Na$_2$SO$_4$, filtered, and concentrated. The crude material was then dissolved with dichloromethane and ethyl acetate, leaving an insoluble gum behind. The solution was purified by column chromatography (EtOAc/hexanes gradient), to yield the title compound as a pale yellow solid (4.10 g, 66%). LRMS (ESI+) (M+H): 291.96.

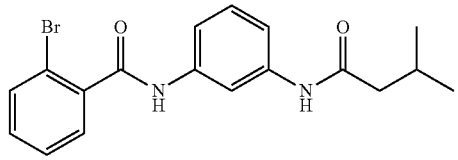

2-bromo-N-(3-(3-methylbutanamido)phenyl)benzamide

N-(3-Aminophenyl)-2-bromobenzamide (50 mg, 0.17 mmol), dichloromethane (1.7 mL), pyridine (17 μL, 0.21 mmol), and isovaleryl chloride (25 μL, 0.21 mmol) were added to a vial with stir bar and stirred for 20 h. The reaction was then diluted with ethyl acetate, then the combined organics were washed with 1 M aqueous HCl, then half-saturated aqueous NaHCO3, then brine. The crude solution was dried over Na$_2$SO$_4$, filtered, and concentrated to a colorless oil, then purified by column chromatography (EtOAc/hexanes gradient) after dry-loading on SiO$_2$. The title compound was obtained as a white solid (53 mg, 82%). LRMS (ESI+) (M+H): 375.05.

2-bromo-N-(3-(butylamino)phenyl)benzamide

N-(3-Aminophenyl)-2-bromobenzamide (100 mg, 0.34 mmol) was added to a 10 mL vial with stir bar and dissolved with 1,2-dichloroethane (1.7 mL). Butyraldehyde (46 µL, 0.52 mmol) was added by syringe, followed by sodium triacetoxyborohydride (182 mg, 0.86 mmol). The reaction was stirred for 2 h, after which time LC-MS analysis showed a mixture of mono- and dialkylated material, with little or no aniline starting material remaining. The reaction was quenched by adding aqueous $NaHCO_3$ and stirring well until bubbling ceased. The crude mixture was diluted with ethyl acetate and water, the layers were separated, then the organic phase was washed again with aq. $NaHCO_3$, then brine. The combined organics were dried over $Na_2SO_4$, filtered, and concentrated to a pale yellow oil, then purified by column chromatography (EtOAc/hexanes gradient) to yield a pink oil. This was redissolved with ether/dichloromethane, then the HCl salt of the desired product was formed by adding excess 2 M HCl in ether. The supernatant was removed from the resulting solid, which was subsequently pulverized and washed three times with ether (~1 mL), then dried. The title compound (HCl salt) was obtained as an off-white solid (41 mg, 33%). LRMS (ESI+) (M+H): 349.42.

The compounds were tested in two independent $IC_{50}$ determination experiments using the primary assay measuring SFLLRN-mediated granule secretion. For this assay, platelet-rich plasma is treated with putative inhibitors prior to activation by the SFLLRN peptide, which targets the Par1 (thrombin) receptor. Upon activation, platelets secrete dense granules, which are concentrated with ATP. Platelet activation and possible inhibition are monitored by a luciferin-luciferase assay (CellTiter-Glo without lysis reagent) to measure the ATP secreted from activated platelets. Luminescence measurements are made using a plate reader (Envision, PerkinElmer) capable of detecting luminescence. The $IC_{50}$ values for the two retests of the probe were 4.87 µM and 5.28 µM.

Compound-1 showed 90% inhibition of the expression of P-selectin at 1 µM of the compound, upon activation with SFLLRN when tested in an assay using washed platelets. For this assay, the probe is incubated with washed platelets obtained from individual donors. Platelets are subsequently stimulated with 5 µM SFLLRN. After 15 minutes, phyco-erythrin-labeled anti-P-selectin antibody (BD Biosciences) is added to the incubation mixture. Following a 20-minute incubation, a sample is analyzed by flow cytometry for staining of P-selectin.

Compound-1 demonstrated inactivity for the modulation of cAMP production at 10 µM. For this assay, platelets obtained from individual donors were washed and incubated with the probe. Platelets exposed to PGE1 (which causes elevation of platelet cAMP levels) are used as controls. Following incubation, platelets are lysed and evaluated in a commercially available competitive immunoassay of cAMP. Compounds that raise cAMP levels less than 50% of that of PGE1 are considered negative in this assay.

Finally, the Compound-1 did not show any effect on PMA-induced or Ca2+ ionophore-induced activation of platelets. For these assays, the probe is incubated with washed platelets obtained from individual donors in a 6 point dose curve. Platelets are subsequently stimulated with either PMA or Ca2+ ionophore. After 15 minutes, phyco-erythrin-labeled anti-P-selectin antibody (BD Biosciences) is added to the incubation mixture. Following a 20-minute incubation, a sample is analyzed by flow cytometry for staining of P-selectin.

These compounds demonstrate several characteristics that distinguish them from orthosteric inhibitors of Par1. They inhibit platelet secretion and aggregation without inhibiting platelet shape change, suggesting that they spare Galpha12/13 signaling.

The measured $IC_{50}$ activity of the compounds are categorized as I (0.001 µM-1 µM), II (>1 µM-5 µM), III (>5 µM-10 µM) and IV (>10 µM).

TABLE D

| Compound | Activity |
|---|---|
|  | I |
|  | II |
|  | II |
|  | IV |
|  | IV |

TABLE D-continued

| Compound | Activity |
|---|---|
| [4-(trifluoromethyl)benzamide, N-(3-butyramidophenyl)] | IV |
| [biphenyl-3-carboxamide, N-(3-butyramidophenyl)] | (none) |
| [3-cyanobenzamide, N-(3-butyramidophenyl)] | (none) |
| [3-phenoxybenzamide, N-(3-butyramidophenyl)] | (none) |
| [4-chlorobenzamide, N-(3-butyramidophenyl)] | (none) |
| [4-methoxybenzamide, N-(3-butyramidophenyl)] | IV |
| [4-(methylsulfonyl)benzamide, N-(3-butyramidophenyl)] | IV |
| [2-methylbenzamide, N-(3-butyramidophenyl)] | I |
| [3-chlorobenzamide, N-(3-butyramidophenyl)] | (none) |

TABLE D-continued

| Compound | Activity |
|---|---|
| [2-fluorobenzamide, N-(3-butyramidophenyl)] | I |
| [2-chlorobenzamide, N-(3-butyramidophenyl)] | II |
| [nicotinamide, N-(3-butyramidophenyl)] | IV |
| [quinoline-3-carboxamide, N-(3-butyramidophenyl)] | IV |
| [furan-2-carboxamide, N-(3-butyramidophenyl)] | IV |
| [4-methylbenzamide, N-(3-butyramidophenyl)] | IV |
| [3-(methylsulfonyl)benzamide, N-(3-butyramidophenyl)] | IV |
| [4-fluorobenzamide, N-(3-butyramidophenyl)] | IV |
| [2-bromobenzamide, N-(3-isobutyramidophenyl)] | (none) |

TABLE D-continued

| Compound | Activity |
|---|---|
| cyclopentyl-C(O)NH-(1,3-phenylene)-NHC(O)-(2-Br-phenyl) | I |
| Ph-C(O)NH-(1,3-phenylene)-NHC(O)-(2-Br-phenyl) | IV |
| n-Pr-C(O)NH-(pyridine-2,4-diyl)-NHC(O)-(2-Br-phenyl) | IV |
| cyclopentyl-C(O)NH-(pyridine-2,4-diyl)-NHC(O)-(2-Br-phenyl) | IV |
| Ph-C(O)NH-(pyridine-2,4-diyl)-NHC(O)-(2-Br-phenyl) | IV |
| n-Pr-C(O)NH-(1,3-phenylene)-N(Me)C(O)-(2-Br-phenyl) | IV |
| cyclopentyl-C(O)NH-(1,3-phenylene)-N(Me)C(O)-(2-Br-phenyl) | IV |
| Ph-C(O)NH-(1,3-phenylene)-NHC(O)-n-Pr | IV |
| n-Pr-C(O)NH-(1,4-phenylene)-NHC(O)-(2-Br-phenyl) | IV |
| n-Pr-C(O)NH-(1,3-phenylene)-NHC(O)-(2-CF₃-phenyl) | II |
| (2-OCF₃-phenyl)-C(O)NH-(1,3-phenylene)-NHC(O)-n-Pr | I |
| (2-(NMe₂C(O))-phenyl)-C(O)NH-(1,3-phenylene)-NHC(O)-n-Pr | IV |
| (biphenyl-2-yl)-C(O)NH-(1,3-phenylene)-NHC(O)-n-Pr | IV |
| (2-Et-phenyl)-C(O)NH-(1,3-phenylene)-NHC(O)-n-Pr | I |
| (2,6-diMe-phenyl)-C(O)NH-(1,3-phenylene)-NHC(O)-n-Pr | II |
| (2-Br-phenyl)-C(O)NH-(1,3-phenylene)-N(Me)C(O)-n-Pr | IV |
| iso-Bu-C(O)NH-(1,3-phenylene)-NHC(O)-(2-Br-phenyl) | I |

TABLE D-continued

| Compound | Activity |
|---|---|
| (ethyl carbamate - 3-aminophenyl - NH - C(O) - 2-bromophenyl) | II |
| (2-methylbenzamide - 3-aminophenyl - NH - C(O)CH2CH(CH3)2) | II |
| (butyramide - 4-chloro-3-aminophenyl - NH - C(O) - 2-methylphenyl) | IV |
| (butyramide - 4-chloro-3-aminophenyl - NH - C(O) - 2-bromophenyl) | IV |
| (2-methylbenzamide - 4-methyl-3-aminophenyl - NH - C(O)CH2CH3) | IV |
| (butyramide - 3-aminophenyl - C(O)NH - 2-chlorophenyl) | IV |
| (2-chlorobenzamide - 3-aminophenyl - C(O)NH - propyl) | II |
| (butylamine - 3-aminophenyl - NH - C(O) - 2-bromophenyl) HCl | I |
| (butyramide - 3-aminophenyl - NH - CH2 - 2-bromophenyl) HCl | IV |
| (2-methylsulfonylbenzamide - 3-aminophenyl - NH - C(O)CH2CH2CH3) | IV |
| (butyramide - 3-aminophenyl - NH - C(O) - 2-bromo-5-methylphenyl) | I |
| (butyramide - 3-aminophenyl - NH - C(O) - 2-bromo-4-fluorophenyl) | I |
| (butyramide - 3-aminophenyl - NH - C(O) - 2-bromo-5-fluorophenyl) | I |
| (butyramide - 3-aminophenyl - NH - C(O) - 2-bromo-5-chlorophenyl) | I |
| (2,2-dimethylbutanamide - 3-aminophenyl - NH - C(O) - 2-bromophenyl) | IV |
| (2,3-dichlorobenzamide - 3-aminophenyl - NH - C(O)CH2CH2CH3) | II |
| (2-bromo-6-chlorobenzamide - 3-aminophenyl - NH - C(O)CH2CH2CH3) | II |

Compound 1's effect on PAR1-mediated signaling and on thrombus formation were studied. These results indicate that compound 1 blocks PAR1 via a non-orthosteric mechanism and potently inhibits both platelet accumulation and fibrin generation that occurs during thrombus formation at sites of vascular injury. These data demonstrate that the compound 1 inhibits PAR1 activity via a novel mechanism and demonstrates the efficacy of compound 1 in a pre-clinical model.

To confirm the specificity of compound 1 for PAR1, platelets were incubated with compound 1 and subsequently activated with a variety of platelet agonists. P-selectin surface expression was monitored to detect platelet activation. The results in FIG. 1A demonstrate that compound 1 inhibits activation mediated through PAR1 with an $IC_{50}$ of approximately 300 nM. In contrast, an $IC_{50}$ for inhibition of other agonists was not reached even at concentrations >30-fold its $IC_{50}$ for PAR1-mediated secretion. To further evaluate whether PAR1 is the target of compound 1, we tested the ability of the compound to inhibit $Ca^{2+}$ flux in HEK293 cells overexpressing recombinant PAR1. These studies show that compound 1 inhibits changes in $Ca^{2+}$ flux in these cells at concentrations similar to those required for inhibition of PAR1-mediated P-selectin surface expression (FIG. 1B). In contrast, compound 1 fails to inhibit P-selectin surface expression induced by GTP-γ-S in permeabilized platelets (FIG. 1C). These results confirm that compound 1 acts proximally in the PAR1-mediated signaling pathway.

Figure 2:
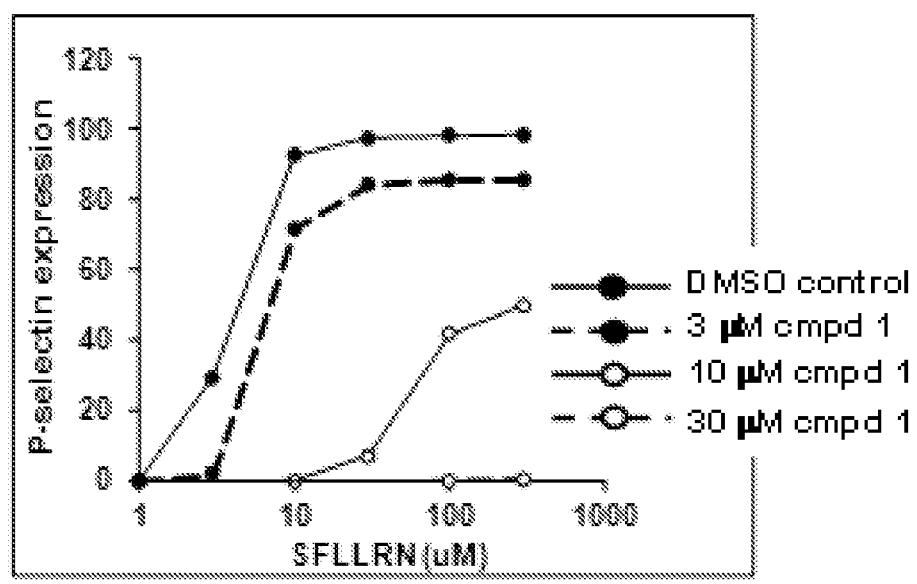
FIG. 2: Compound-1 demonstrates non-competitive inhibition of PAR1-mediated platelet activation.

Compound-1 demonstrates non-competitive inhibition of PAR1-mediated platelet activation: Platelets were incubated with varying concentrations of Compound-1 and subsequently stimulated with the varying concentrations of (indicated in FIG. 2) SFLLRN. The resultant pattern of inhibition is consistent with non-competitive inhibition of PAR1.

Figure 3:
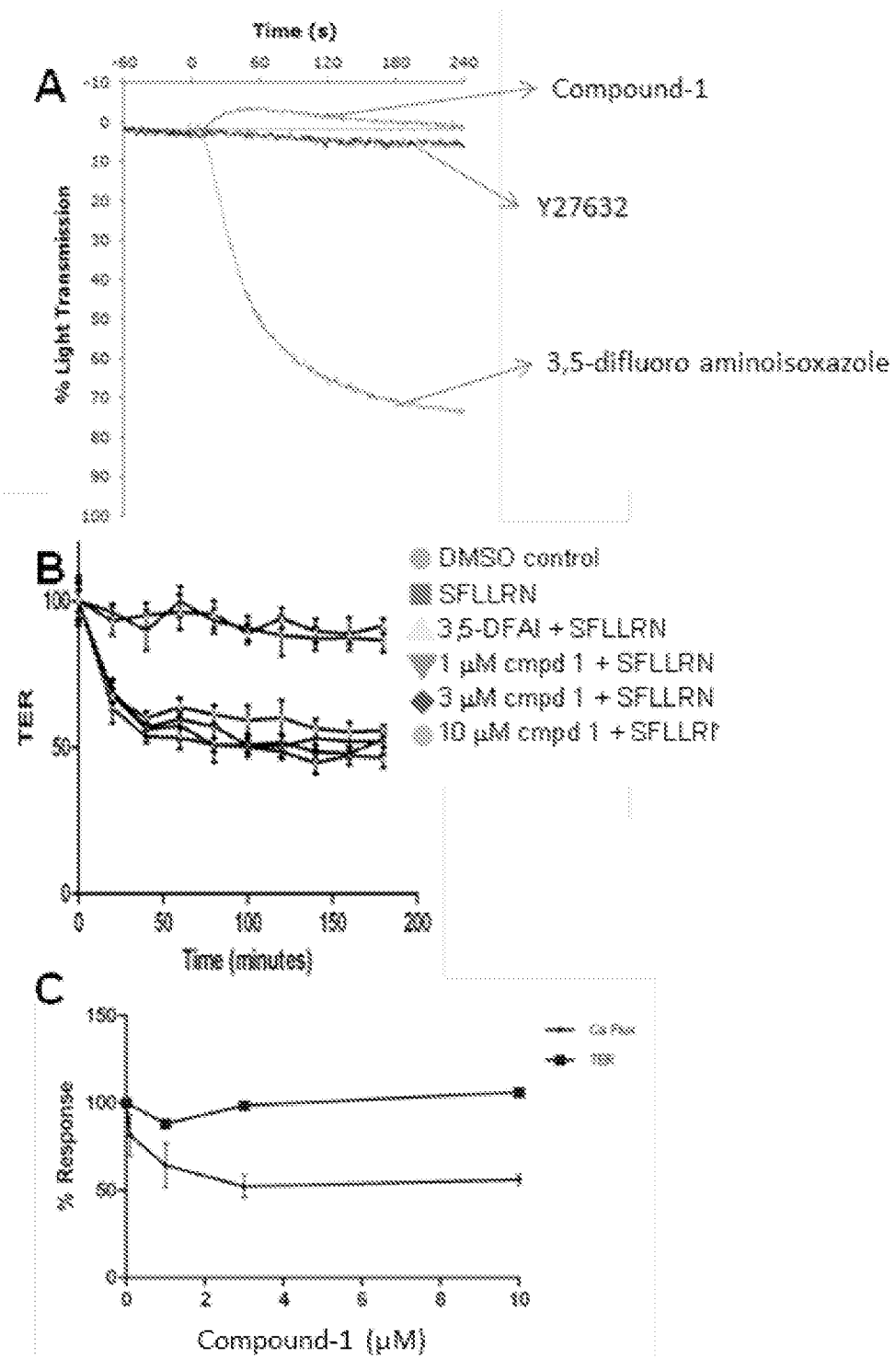
FIG. 3: Compound-1 inhibits Gαq, but not Gα$_{12}$, downstream of PAR1 activation. (A) Compound-1 blocks platelet aggregation, but not shape change. Both aggregation and shape change are inhibited in the presence of Compound-1 plus Y27632 (CAS Number: 331752-47-7) or 3,5-difluoro aminoisoxazole. Compound 1 fails to inhibit SFLLRN-induced TER in MDCK cells (B), but inhibits SFLLRN-induced Ca2+ flux (C).

Evaluation of multiple dose curves using the P-selectin surface expression-based assay (FIG. 3) demonstrates saturable inhibition of platelet activation mediated through PAR1. This pattern of inhibition is consistent with that of an allosteric inhibitor. Compound 1 also inhibited PAR1-mediated platelet aggregation (FIG. 3A). However, it failed to inhibit PAR1-mediated platelet shape change. This observation raised the possibility that compound 1 blocks PAR1 signaling through $G_{\alpha q}$ (which mediates platelet aggregation downstream of PAR1), but not $G_{\alpha 12/13}$ (which mediates shape change downstream of PAR1). A previously identified PAR1 inhibitor, 3,5-difluoro aminoisoxazole (3,5-DFAI), inhibited both shape change and aggregation. Shape change that occurred in the presence of compound 1 was blocked by the Rho kinase inhibitor Y27632, confirming participation of Rho kinase downstream of $G_{\alpha 12/13}$ in compound-1-resistance shape change (FIG. 3A). To further evaluate the possibility that compound 1 activity does not inhibit PAR1 signaling through $G_{\alpha 12/13}$, compound 1 was evaluated for its ability to inhibit PAR1-mediated elevation of transmembrane resistance (TER) in MDCK cells overexpressing $G_{\alpha 12}$. PAR1-mediated decrease in TER in these cells is dependent on $G_{\alpha 12}$. Compound 1 failed to inhibit PAR1-mediated TER in these cells, confirming that compound 1 does not block $G_{\alpha 12}$ signaling downstream of PAR1 (FIG. 3B). In contrast, 3,5-DFAI inhibited SFLLRN-mediated decrease in TER (FIG. 3B) and compound 1 inhibited $G_{\alpha q}$-mediated $Ca^{2+}$ flux in these MDCK cells (FIG. 3C). These results demonstrate that compound 1 acts via a non-orthosteric mechanism, inhibiting $G_{\alpha q}$-mediated, but not $G_{\alpha 12}$-mediated signaling. Thus, compound 1 demonstrates selectivity at the level of $G_\alpha$ subunit signaling.

Figure 4:
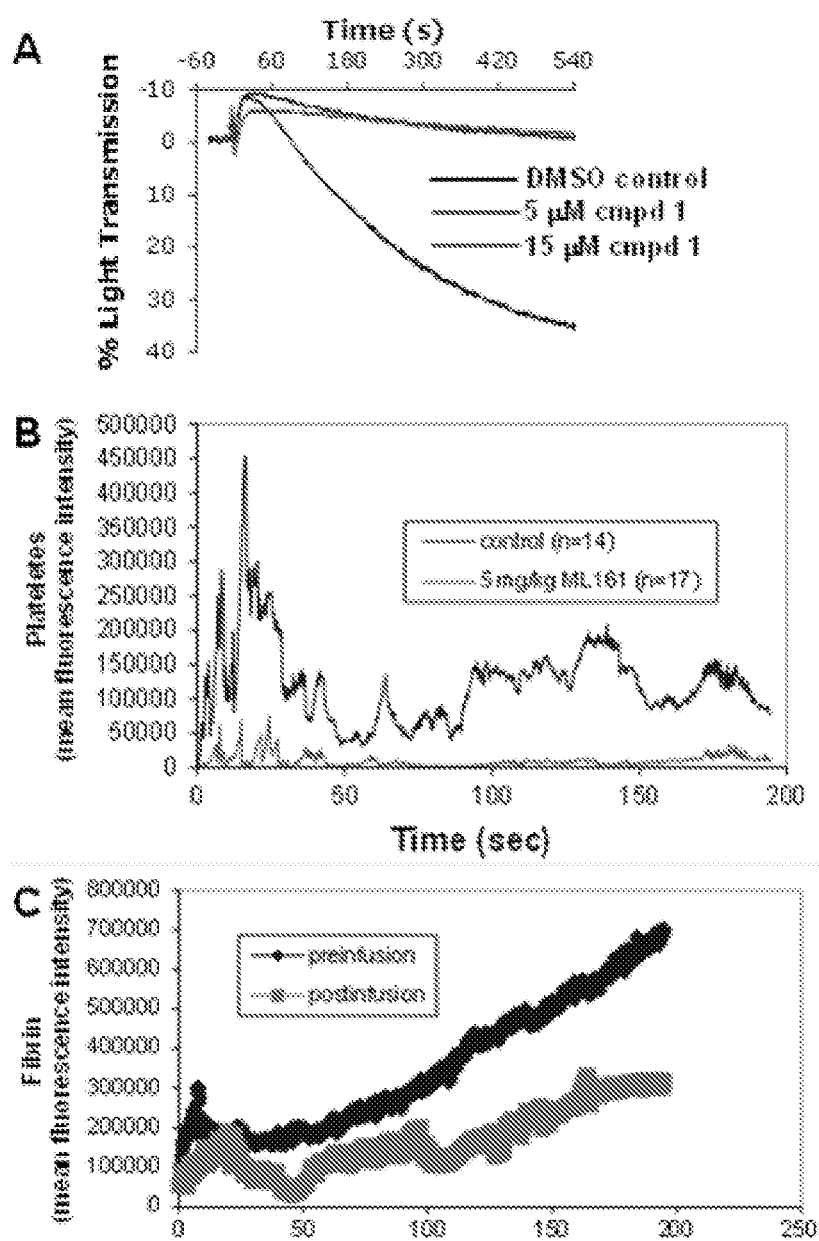
FIG. 4: (A) PAR-4 mediated aggregation of mouse platelets is inhibited by Compound-1. (B) Infusion of 5 mg/kg of Compound-1 blocks platelet accumulation following vascular injury. (C) Infusion of 5 mg/kg of Compound-1 blocks fibrin generation following vascular injury.

In vivo thrombus formation studies:

PAR1 is the thrombin receptor on human platelets and serves an important function in mediating thrombus formation. We tested compound 1 to determine whether it inhibited thrombus formation following laser-induced injury of the cremaster arteriole in mice. The dominant PAR receptor on mouse platelets is PAR4. However, since compound 1 acts at a non-orthosteric site and mouse PAR4 differs from human PAR4, we reasoned that compound 1 may be able to block mouse PAR4. Aggregation studies using mouse platelets demonstrate that compound 1 inhibits PAR4-mediated aggregation of mouse platelets (FIG. 4A). When infused into mice at a concentration of 5 mg/kg, compound 1 inhibited platelet accumulation during thrombus formation by >90% (FIG. 4B). Infusion of 5 mg/kg also impaired fibrin generation during thrombus formation (FIG. 4C). Thus, compound 1 blocks both cellular- and coagulation protein-mediated arms of thrombus formation. It was noted that the antithrombotic activity of compound 1 appeared to abate following approximately 45 min to 1 hour after infusion. The compound was therefore infused every 30 minutes during the course of these experiments. The short half-life of compound 1 in vivo may be useful in scenarios in which anticoagulation is only required for a short period of time or when anticoagulation needs to be reversed quickly, such as anticoagulation prior to invasive procedures or surgery.

Figure 5:
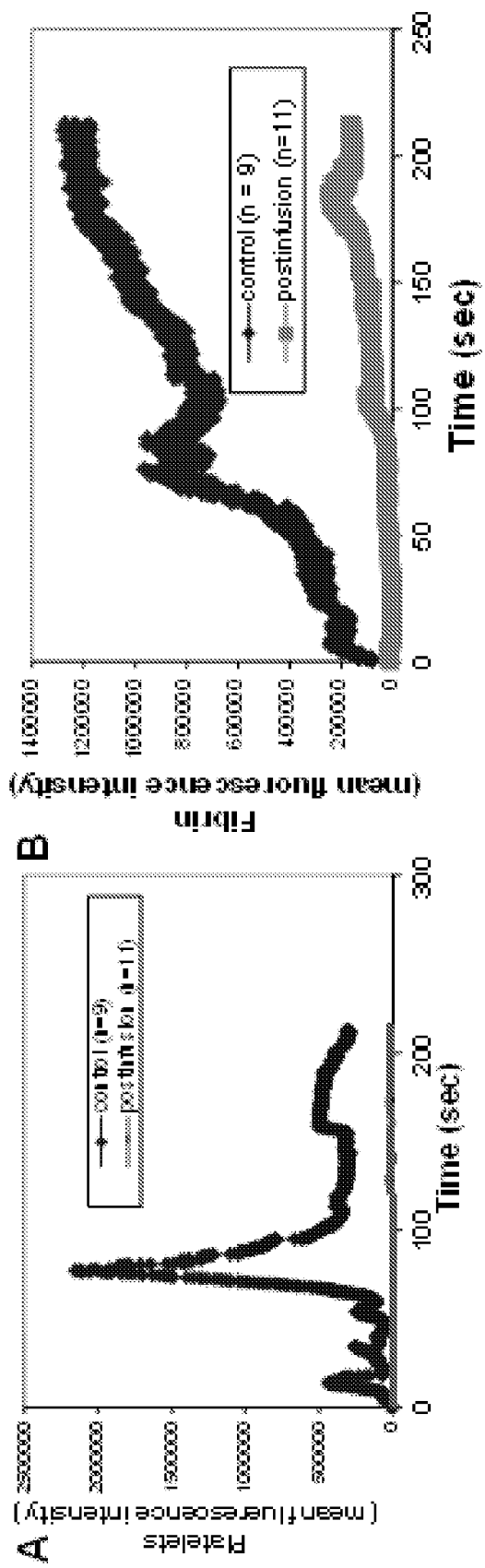
FIG. 5: 2-bromo-N-(3-(3-methylbutanamido)phenyl)benzamide is stable in mouse plasma inhibits thrombus formation following a single bolus infusion. (A) Infusion of 5 mg/kg of Compound-1 blocks platelet accumulation following vascular injury. (B) Infusion of 5 mg/kg of 2-bromo-N-(3-(3-methylbutanamido)phenyl)benzamide also blocks fibrin generation following vascular injury.

Since there are also situations in which longer term anticoagulation is desired, we performed further studies in the thrombus formation model to assess analogs of compound 1 that may have a more long-lived effect. While Compound 1 was not very stable in mouse plasma (with only 1.7% remaining after a 5 hour incubation) it had good stability in human plasma. This instability in mouse plasma may have contributed to its short half-life of efficacy in vivo. In contrast, 2-bromo-N-(3-(3-methylbutanamido)phenyl) benzamide generated had considerably better stability in mouse plasma (64.6% remaining after 5 hour incubation). Following a single infusion of 5 mg/kg of the more stable compound 1 analog into mice, platelet accumulation (FIG. 5A) and fibrin generation (FIG. 5B) during thrombus formation were impaired by >90%. Overall, these thrombus formation studies demonstrate that compound 1 and 2-bromo-N-(3-(3-methylbutanamido)phenyl)benzamide are potent inhibitors of thrombus formation in vivo.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A method of treating a protease-activated receptor (PAR) mediated disease in a patient by administrating a therapeutically effective dose of compound selected from:

TABLE A
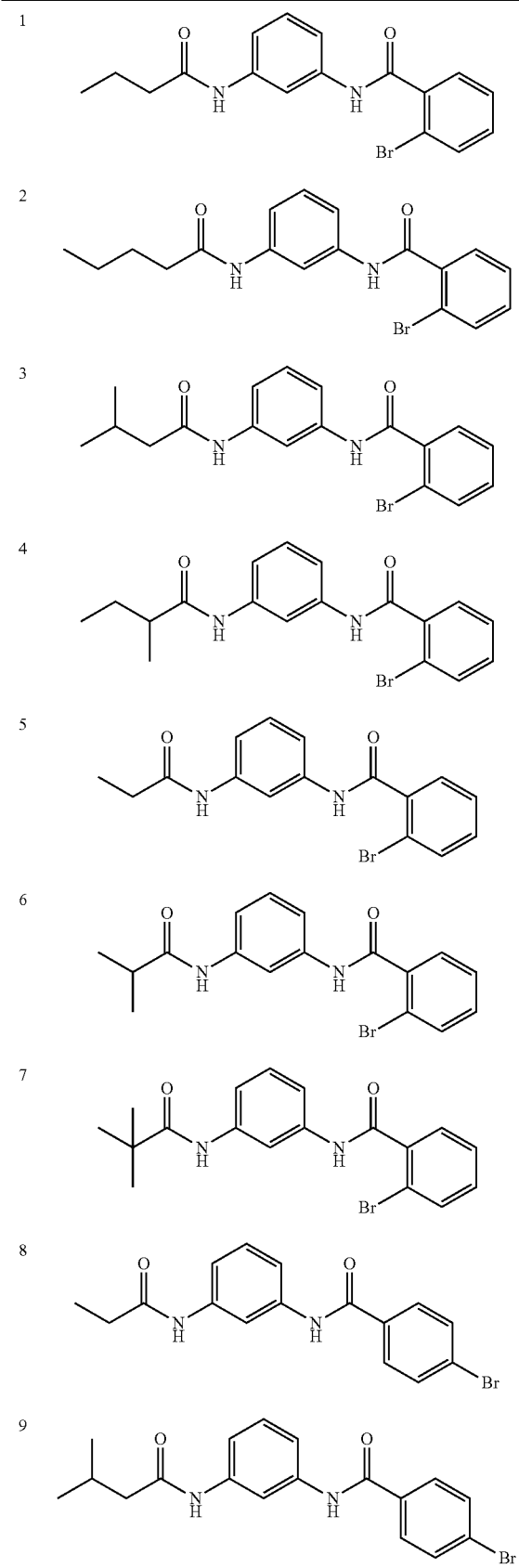
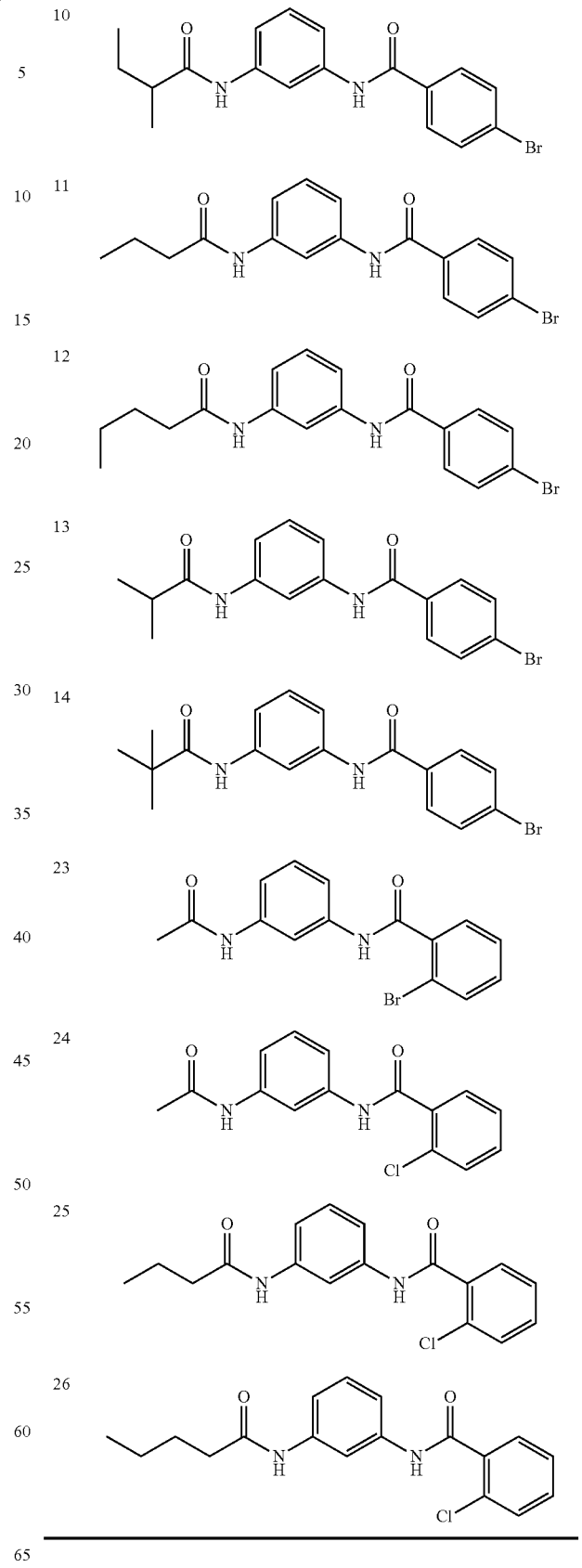
wherein the PAR mediated disease is selected from acute Myocardial Infarction, acute occlusion following coronary angioplasty or stent placement thrombosis subsequent to or associated with a surgical procedure, and thrombosis associated with atrial fibrillation.

2. The method of claim 1, wherein the patient is in need of inhibition of platelet activation.

3. The method of claim 1, wherein the patient is in need of inhibition of thrombus formation.

4. The method of claim 1, wherein said PAR mediated disease is acute Myocardial Infarction.

5. The method of claim 1, wherein said PAR mediated disease is acute occlusion following coronary angioplasty or stent placement.

6. The method of claim 1, wherein said PAR mediated disease is thrombosis subsequent to or associated with a surgical procedure.

7. The method of claim 1, wherein said PAR mediated disease is thrombosis associated with atrial fibrillation.

* * * * *